(12) United States Patent
Langkilde

(10) Patent No.: US 11,826,376 B2
(45) Date of Patent: Nov. 28, 2023

(54) METHODS OF TREATING HEART FAILURE WITH PRESERVED EJECTION FRACTION EMPLOYING DAPAGLIFLOZIN AND COMPOSITIONS COMPRISING THE SAME

(71) Applicant: AstraZeneca AB, Södertälje (SE)

(72) Inventor: Anna Maria Langkilde, Gothenburg (SE)

(73) Assignee: ASTRAZENECA AB, Södertälje (SE)

( * ) Notice: Subject to any disclaimer, the term of this patent is extended or adjusted under 35 U.S.C. 154(b) by 0 days.

(21) Appl. No.: 16/515,086

(22) Filed: Jul. 18, 2019

(65) Prior Publication Data

US 2020/0078382 A1    Mar. 12, 2020

Related U.S. Application Data

(60) Provisional application No. 62/700,463, filed on Jul. 19, 2018.

(51) Int. Cl.
  *A61K 31/70*   (2006.01)
  *A61K 45/06*   (2006.01)

(52) U.S. Cl.
  CPC .............. *A61K 31/70* (2013.01); *A61K 45/06* (2013.01)

(58) Field of Classification Search
  None
  See application file for complete search history.

(56) References Cited

U.S. PATENT DOCUMENTS

| | | | |
|---|---|---|---|
| 9,394,291 B2 | 7/2016 | O'Mahony | |
| 10,973,836 B2 | 4/2021 | Langkilde | |
| 2008/0058379 A1* | 3/2008 | Eckhardt | A61P 1/18 514/326 |
| 2017/0266152 A1 | 9/2017 | Broedl et al. | |
| 2019/0192482 A1 | 6/2019 | Minamino | |
| 2020/0054656 A1 | 2/2020 | Kim | |
| 2020/0078382 A1 | 3/2020 | Langkilde | |
| 2021/0060043 A1 | 3/2021 | Langkilde | |
| 2021/0260083 A1 | 8/2021 | Langkilde | |

FOREIGN PATENT DOCUMENTS

| KR | 10-2015-0138859 | 12/2015 |
|---|---|---|
| KR | 10-2018-122004 | 11/2018 |
| KR | 10-1943382 | 1/2019 |
| WO | WO 2014/161918 A1 | 10/2014 |
| WO | WO 2017/157816 A1 | 9/2017 |
| WO | WO 2018/142422 | 8/2018 |
| WO | WO 2019/059557 | 3/2019 |
| WO | 2020016335 A1 | 1/2020 |

OTHER PUBLICATIONS

History of changes for Study NCT02751398, version Aug. 25, 2016. (Year: 2016).*
History of changes for Study NCT03036124, version Jan. 26, 2017. (Year: 2017).*
Riggs, .etabolic Syndrome and Related Disorders, vol. 13, No. 7, 2015, pp. 292-297. (Year: 2015).*
Gandhi, What's a "Normal" A1C? When is it Misleading? Internet article, https://diatribe.org/whats-normal-a1c-when-it-misleading, Oct. 31, 2017. (Year: 2017).*
History of changes for Study NCT03030235 (version Jan. 20, 2017. (Year: 2017).*
Urbanek, et al., "Dapagliflozin ameliorates diastolic function in an animal model of hypertensive heart disease in the absence of diabetes", European Journal of Heart Failure, May 2018, vol. 20.
Custodio, et al., "SGLT2 inhibition and heart failure-current concepts", Heart Fail Rev., May 2018, vol. 23.
Trang, et al., Treating Disease Mechanisms in Patients With Heart Failure and Diabetes Mellitus, Curr Heart Fail Rep., Dec. 2017, vol. 14.
International Search Report and Written Opinion for International Application No. PCT/EP2019/069323 dated Dec. 5, 2019.
Connelly, et al., "Can We DECLARE a Victory Against Cardio-Renal Disease in Diabetes?", Cell Metab, Dec. 4, 2018;28(6):813-815.
Hallow, et al., "Why do SGLT2 inhibitors reduce heart failure hospitalization? A differential volume regulation hypothesis", Diabetes Obes Metab, Mar. 2018;20(3):479-487.
Wiviott, et al., "The design and rationale for the Dapagliflozin Effect on Cardiovascular Events (DECLARE)—TIMI 58 Trial", American Heart Journal, vol. 200, Jun. 2018, pp. 83-89.
Akerblom, A et al. (2019), "Effects of DAPAgliflozin on CARDiac substrate uptake, myocardial efficiency, and myocardial contractile work in type 2 diabetes patients—a description of the DAPACARD study," *UPSALA Journal of Medical Sciences*; 124(1): 59-64.
Bhatt, D.L., et al. (2019), "the DAPA-HF Trial: A Momentous Victory in the War against Heart Failure," *Cell Metab*; 30(5): 847-849.
Chemical Abstracts Registry No. 1850385-64-6, AZD9977 (Year: 2016).
Clinical Study Protocol Study to Evaluate the Effect of Dapagliflozin on the Incidence of Worsening Heart Failure or Cardiovascular Death in Patients with Chronic Heart Failure with Reduced Ejection Fraction, Study Code D166C00001. Version 2.0., dated Oct. 26, 2017 (https://www.clinicaltrials.gov/ProvidedDocs/24/NCT03036124/Prot_000.prf).
"Dapagliflozin for chronic heart failure with reduced ejection fraction," Health Technology Briefing May 2019, NIHR Innovation Observatory (7 pages).
Docherty, K. F. et al. (2020), "Effects of dapagliflozin in DAPA-HF according to backgroun heart failure therapy," *Eur. Heart J*; doi: 10.1093/eurheartj/ehaa183 (14 pages).
"Farxiga met primary endpoint in landmark Phase III DAPA-HF trial for the treatment of patients with heart failure," published Aug. 20, 2019 (3 pages) (https://www.astrazeneca.com/media-centre/press-releases/2019/farxiga-met-primary-endpoint-in-landmark-phase-iii-dapa-hf-trial-for-the-treatment-of-patients-with-heart-failure-20082019.html).

(Continued)

*Primary Examiner* — Layla D Berry
(74) *Attorney, Agent, or Firm* — Finnegan, Henderson, Farabow, Garrett & Dunner, LLP

(57) ABSTRACT

Methods for treating and/or preventing HFpEF and/or at least one disease, disorder, and/or condition associated therewith in patients by the use of dapagliflozin and compositions comprising the same are disclosed.

27 Claims, 1 Drawing Sheet

(56) References Cited

OTHER PUBLICATIONS

Fitchett et al., "Heart failure outcomes with empagliflozin in patients with type 2 diabetes at high cardiovasular risk: results of the EMPA-REG OUTCOME® trial," Eur Heart J, 2016; 37: 1526-1534.
Furtado, R. H. M. et al. (2019), "Dapagliflozin and Cardiovascular Outcomes in Patients with Type 2 Diabetes Mellitus and Previous Mycardial Infarction," Circulation; 139(22):2516-2527.
Green et al., "Development and Evaluation of the Kansas City Cardiomyopathy Questionnaire: A New Health Status Measure for Heart Failure" Journal of the American College of Cardiology, vol. 35, No. 5. pp. 1245-1255 (Year: 2000).
History of changes for Study NCT03036124, version Jan. 10, 2019.
Jensen, J. et al., "Empagliflozin in heart failure patients with reduced ejection fraction: a randomized clinical trial (Empire HF)," Trials (2019) 20:374 (8 pages).
Joseph et al., "Acute Decompensated Heart Failure," Texas Heart Institute Journal, vol. 36, No. 6, pp. 510-520 (Year: 2009).
Kalra, S. "Cardiorenal syndromes and SGLT2 inhibitor usage," Medicine Matters Diabetes—Aug. 6, 2019 (5 pages).
Kaplinsky, E. (2020), "DAPA-HF trial: dapagliflozin evolves from a glucose-lowering agent to a therapy for heart failure" Drugs Context; 9: doi: 10.7573/dic.2019-11-3 (7 pages).
Kato, E. T. et al. (2020) "Effects of Dapagliflozin on Heart Failure and Mortality in Type 2 Diabetes Mellitus," Circulation; 139(22): 2528-2536.
Komajda et al., "Heart failure events with rosiglitazone in type 2 diabetes: data from the RECORD clinical trial," Eur Heart J, 2010; 31: 824-831.
Kosiborod, M. N. et al. (2020), "Effects of Dapagliflozin on Symptoms, Function, and Quality of Life in Patients with Heart Failure and Reduced Ejection Fraction: Results from the DAPA-HF Trial," Circulation; 141(2): 90-99.
Kosiborod, M. M.D. et al. (2017), "Lower Risk of Heart Failure and Death in Patients Initiated on Sodium-Glucose Cotransporter-2 Inhibitors Versus Other Glucose-Lowering Drugs: The CVD-REAL Study (Comparative Effectiveness of Cardiovascular Outcomes in New Users of Sodium-Glucose Cotransporter-2 Inhibitors)," Circulation, 136- 249-259, DOI: 10.1161/CIRCULATIONAHA.117.029190 (92 pages, including supplemental material).
Lago et al., "Congestive heart failure and cardiovascular death in patients with prediabetes and type 2 diabetes given thiazolidinediones: a meta-analysis of randomized clinical trials," Lancet, 2007; 370: 1129-1136.
Lan et al., "The effects of sodium-gucose cotransporter 2 inhibitors on left ventricular function: current evidence and future directions," ESC Heart Failure, 2019; 6: 927-935.
Laure et al., "Role of senescence mechanisms in the transitions from cardia hypertrophy to heart failure in H11K-transgenic mouse" Archives of Cardiovascular Diseases Supplements, vol. 2, p. 19, abstract 0354 (Year: 2012).
Mahaffey et al., "Canagliflozin for primary and secondary prevention of cardiovascular events: results from the CANVAS Program ( Canagliflozin Cardiovascular Assessment Study)," Circulation, 2018; 137:323-334.
Martinez, F. A. et al., (2020), "Efficacy and Safety of Dapagliflozin in Heart Failure with Reduced Ejection Fraction According to Age: Insights from DAPA-HF," Circulation; 141(2):100-111.
Mayo Clinic article, "Arterioscerosis/Atherosclerosis" download from https://www.mayoclinic.org/diseases-conditions/artheriosclerosis-atherosclerosis/symptomscauses/syc-20350569?p=1 (Year: 2018).
McMurray, J. J. V. et al. (2019), "The Dapagliflozin and Prevention of Adverse-outcomes in Heart Failure (DAPA-HF) trial: baseline characteristics," Eur J Heart Fail; 21(11): 1402-1411.
Mc Murray, J. J. V. et al. (2019), "A trial to evaluate the effect of the sodium-glucose co-transporter 2 inhibitor dapagliflozin on morbidity and mortality in patients with heart failure and reduced left ventricular ejection fraction (DAPA-HF),"Eur J Heart Fail 21(5): 665-675.
McMurray, J. J. V. et al. (2020), "The Dapagliflozin and Prevention of Adverse Outcomes in Heart Failure Trial (DAPA-HF) in context," Eur Heart J; doi: 10.1093/eurheartj/ehz916 (4 pages).
McMurray, J. J. V. et al. (2019), "Dapaglioflozin in Patients with Heart Failure and Reduced Ejection Fraction," N Engl J Med; 381(21): 1995-2008.
Nassif, M.E. et al. (2019), "Dapaglioflozin Effects on Biomarkers, Symptoms, and Functional Status in Patients with Heart Failure Ejection Fraction: The DEFINE-HF Trial," Circulation; 140(18): 1463-1476.
Neal, B., M.D. et al. (2017), "Canagliflozin and Cardiovascular and Renal Events in Type 2 Diabetes," N Engl J Med; 377: 644-657.
Oh, C. et al., "Cardioprotective Potential of an SGLT2 Inhibitor Against Doxorubicin-Induccced Heart Failure," Korean Circulation Journal, Dec. 2019; 49(12):1183-1195.
Oldgren, J. et al. (Mar. 24, 2020), "Effects of 6 Weeks of Treatment with Dapagliflozin, a Sodium-Glucose Co-Transporter 2 Inhibitor, on Myocardial Function and Metabolism in Type 2 Diabetes Patients: A Randomized Placebo-Controlled Study," ACC.20, Poster Abstract; JACC; 75(11): Presentation Number 1112-210.
Packer et al., "Effects of sodium-glucose contransporter 2 inhibitors for the treatment of patients with heart failure: proposal of a novel mechanism of action," JAMA Cardiol, 2017; 2: 1025-1029.
Packer et al., "Evaluation of the effect of sodium-glucose co-transporter 2 inhibition with empagliflozin on morbidity and mortality of patients with chronic heart failure and a reduced ejection fraction: rationale for design of the EMPEROR-Reduced trial," European Journal of Heart Failure, 2019; 21: 1270-1278.
Packer, M. (2019), "Lessons learned from the DAPA-HF trial concerning the mechanisms of benefit of SGLT1 inhibitors on heart failure events in the context of other large-scale trials nearing completion," Cardiovasc Diabetol; 18(1): 129 (4 pages).
Petrie, M. C. et al. (2020), "Effect of Dapagliflozin on Worsening Heart Failure and Cardiovascular Death in Patients with Heart Failure with and without Diabetes," Jama; 323(14): 1353-1368.
Raut et al., "miR-30c and miR-181a synergistically modulate p53-p21 pathway in diabetes induced cardiac hypertrophy" Molecular and Cellular Biochemistry, vol. 417, pp. 191-203 (Year: 2016).
Sano, M. et al., "A new class of drugs for heart failure: SGLT2 inhibitors reduce sympathetic overactivity." Journal of Cardiology, 71 (2018), 471-476.
Correction to Scirica et al., "Heart failure, saxagliptin, and diabetes mellitus: observations from the SAVOR-TIMI 53 randomized trial," Circulation, 2015; 132: e198 (1 page).
Sattar et al., "SGLT2 inhibition and cardiovascular events: why did EMPA-REG outcomes surprise and what were the likely mechanisms?" Diabetologia, 2016; 59: 1333-1339.
Tanaka et al., "Effects of Sodium Glucose Co-Transporter 2 Inhibitor Canagliflozin in Patients with Type 2 Diabetes and Chronic Heart Failure (CANDLE): An Open-Label, Randomized Controlled Trial," Available at SSRN (2019) (48 pages) htttp://dx.doi.org/10.2139/ssrn.3343659.
Terry, M, "AstraZeneca's Diabetes Drug Farxiga Decreases Heart Failure Risk," Biospace, Aug. 20, 2019 (4 pages).
Verma et al., "The metabolodiuretic promise of sodium-dependent glucose cotransporter 2 inhibition: the search for the sweet spot in the heart failure," JAMA Cardiol, 2017; 2: 939-940.
Verma, S. (2020), "The DAPA-HF trial marks the beginning of a new era in the treatment of heart failure with reduced ejection fraction," Cardiovasc Res; 116(1): e8-e10.
Verma, S. and McMurray, J. J. V. (2019), "The Serendipitous Story of SGLT2 Inhibitors in Heart Failure," Circulation; 139(22): 2537-2541.
Wiviott, S. D. et al. (2019), "Dapagliflozin and Cardiovascular Outcomes in Type 2 Diabetes," N Engl J Med; 380(4): 347-357.
Zannad et al., "Heart failure and mortality outcomes in patients with type 2 diabetes taking alogliptin versus placebo in EXAMINE: a multicentre, randomized, double-blind trial," Lancet, 2015: 385: 2067-2076.

(56) References Cited

OTHER PUBLICATIONS

Zinman, B. M.D. et al. (2015), "Empagliflozin, Cardiovascular Outcomes, and Mortality in Type 2 Diabetes," *N Engl J Med*; 373(22): 2117-2128.

Solomon, SD, et al., "Baseline Characteristics of Patients with HF with Mildly Reduced and Preserved Ejection Fraction," *J Am Coll Cardiol HF*, 2022; 10(3): 184-187.

* cited by examiner

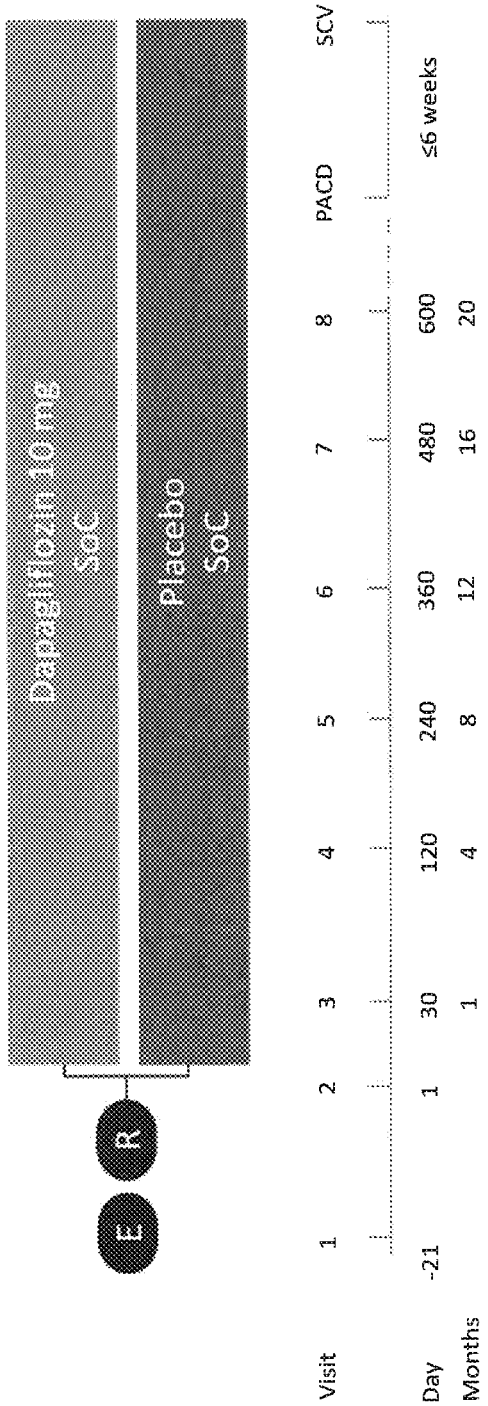

METHODS OF TREATING HEART FAILURE WITH PRESERVED EJECTION FRACTION EMPLOYING DAPAGLIFLOZIN AND COMPOSITIONS COMPRISING THE SAME

Compounds, compositions, and methods for treating heart failure with preserved ejection fraction (HFpEF) in non-diabetic patients are disclosed herein.

Heart failure (HF) is a complex, cardiac syndrome that affects an estimated 38 million people worldwide (Braunwald, Lancet, 385(9970): 812-824 (Feb. 28 2015)), with over 1 million hospitalizations annually in both the United States and Europe (Ambrosy et al., Journal of the American College of Cardiology, 63(2): 1123-1133 (Apr. 1 2014)). HF is characterized by structural and/or cardiac function abnormalities that impair the heart's ability to fill with or eject blood. The clinical syndrome of HF may result from left ventricle (LV) myocardial disease or from LV functional abnormalities. The fundamental manifestations of HF may include dyspnea, fatigue, and/or fluid retention, which may lead to pulmonary congestion and/or peripheral edema (Yancy et al., Circulation, 136:e137-e161. (2017)).

HF can be classified into two subtypes, HF with reduced ejection fraction (HFrEF) and HF with preserved ejection fraction (HFpEF). Ejection fraction (EF or LVEF) is the percentage of the end-diastolic volume of blood ejected from the LV chamber with each heartbeat and thus is a quantitative measure of cardiac function. HFpEF accounts for approximately half of all HF cases and is a leading cause of cardiovascular (CV) morbidity and mortality (Oktay, Rich, and Shaw, Curr Heart Fail Rep., 10(4):10.1007/s11897-013-0155-7 (2013)). The risk of HFpEF mortality is high, with an annual mortality rate up to 15% in community settings (Lam et al., Eur J. Heart Failure, 13:18-28 (2011)). Epidemiologic studies have also found that HFpEF patients are predominantly elderly and female, with a high prevalence of comorbidities such as hypertension, coronary artery disease (CAD), diabetes mellitus (DM), obesity, anemia, chronic kidney disease (CKD), atrial fibrillation, and chronic obstructive pulmonary disease (Fonarow et al., J Am College of Cardiology, 5(8):768-777 (2007)).

Diagnosis and evaluation of patients with HFpEF generally includes imaging of the heart and physical examination, which may provide important information about the severity of structural and/or cardiac abnormalities. Patients with HFpEF have structural heart disease and an EF>40% (Yancy et al. J Am Coll Cardiol, 62(16):1495-539 (2013)). EF may be determined by echocardiography. Additionally, measurement of circulating B-type natriuretic peptide (BNP) and N-terminal proBNP (NT-proBNP), in combination with other comorbidities, may assist in diagnosing HFpEF since these cardiac neurohormones are released by cardiomyocytes in response to LV stretch (Lam & Lim, Cardiology Advisor (2016); Grantham & Burnett, Circulation, 96: 388-390 (1997); Maisel et al., N Engl J Med, 347:161-7 (2002)).

Sodium-glucose co-transporter type 2 (SGLT2) inhibitors are a class of glucose-lowering agents that improve glycemic control with a low risk of hypoglycemia, independent of insulin secretion, providing a reduction in blood pressure, body weight, and levels of uric acid (Inzucchi et al., Diabetes & Vascular Dis Res., 12(2):90-100 (2015)). SGLT2 inhibitors decrease renal glucose reabsorption, thereby increasing urinary glucose excretion (Id.). In addition, SGLT2 inhibitors decrease vascular stiffness and improve endothelial function.

Dapagliflozin is a potent, highly selective and orally active inhibitor of human renal SGLT2 which effectively lowers HbA1c with a low risk of inducing hypoglycaemia. Dapagliflozin treatment has been shown to reduce weight, systolic blood pressure, blood uric acid, albuminuria, and reduces arterial stiffness—all conditions which are associated with increased CV risk (Shigiyama et al., Cardiovasc Diabetol, 16:84 (2017)). The chemical structure of dapagliflozin is:

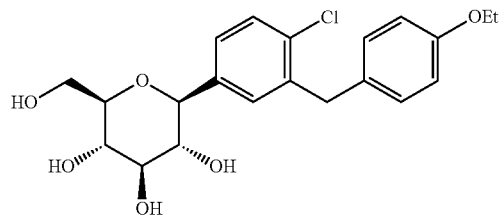 [SMILES: CCOc1ccc(Cc2cc([C@@H]3O[C@H](CO)[C@@H](O)[C@H](O)[C@H]3O)ccc2Cl)cc1]

Recent data from CV outcome trials of SGLT2 inhibitors empagliflozin and canagliflozin and real-world studies including patients treated with dapagliflozin indicate that SGLT2 inhibitors can reduce the risk of CV death and hospitalization due to HF in patients with Type 2 diabetes (T2D) and HF but little is known about the effect SGLT2 inhibitors may have on a non-diabetic patient population (Packer, Diabetes Obes Metab, 20:1361-1366 (2018)). Limitations associated with the randomized clinical trials as well as the observational studies are that only patients with T2D were studied, and that the proportion of patients with reduced ejection fraction (HFrEF) and HFpEF, respectively, is unknown.

There are no proven, effective treatments for HFpEF that reduce the risk for outcomes like hospitalization or death from HF. The current standard of care includes controlling physiological factors, such as. blood pressure, heart rate, blood volume, and myocardial ischemia (Yancy et al., Circulation, 136:e137-e161. (2017); Litwin and Grossman, JACC, 22(4):49A-55A (1993)). Thus, there remains a need for improved compounds, compositions, and methods for treating HFpEF. The present invention addresses these unmet needs.

BRIEF DESCRIPTION OF THE DRAWINGS

FIG. 1 is a diagram illustrating the general study design of Example 1.

DETAILED DESCRIPTION OF THE INVENTION

Briefly stated, methods for treating and/or preventing HFpEF and/or at least one disease, disorder, and/or condition associated therewith are disclosed, the method comprising administering to a patient in need thereof a therapeutically effective amount of at least one compound chosen from compounds of Formula (I)

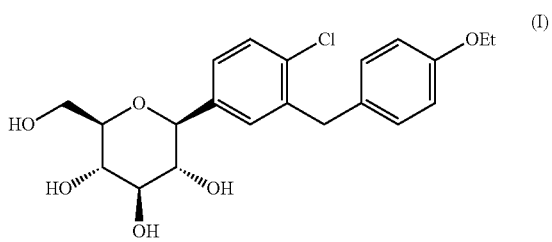 [SMILES: CCOc1ccc(Cc2cc([C@@H]3O[C@H](CO)[C@@H](O)[C@H](O)[C@H]3O)ccc2Cl)cc1]

and prodrugs thereof.

In some embodiments, the method is a method for treating HFpEF.

In some embodiments, the at least one compound chosen from compounds of Formula (I). In some embodiments, the at least one compound is in the form of a pharmaceutically acceptable solvate, mixed solvate, or complex. In some embodiments, the at least one compound is in the form of a non-crystalline solid. In some embodiments, the at least one compound is in the form of a crystalline solid.

In some embodiments, the at least one compound is in the form of a (S)-propylene glycol ((S)-PG) solvate which has the structure shown below:

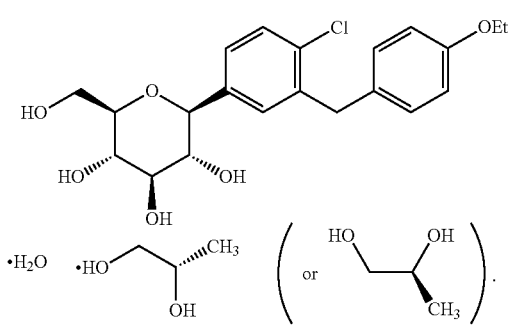

In some embodiments, the at least one compound is in the form of a crystalline S-PG solvate. Methods for preparing a (S)-PG solvate of dapagliflozin, including a crystalline S-PG solvate, are provided in U.S. Pat. No. 7,919,598.

In some embodiments, the method comprises administering to a patient in need thereof a pharmaceutical composition comprising a therapeutically effective amount of at least one compound chosen from compounds of Formula (I) and prodrugs thereof alone or in combination with at least one other therapeutic agent.

In some embodiments, the method comprises administering to a patient in need thereof a pharmaceutical composition comprising a therapeutically effective amount of (1) at least one compound chosen from compounds of Formula (I) and prodrugs thereof and (2) at least one other therapeutic agent.

In some embodiments, the at least one other therapeutic agent is chosen from antidiabetic agents, anti-obesity agents, anti-hyperlipidemic agents, anti-atherosclerotic agents, anti-hypertensive agents, anti-platelet agents, antithrombotic agents, and anticoagulant agents.

In some embodiments, the at least one other therapeutic agent is chosen from antidiabetic agents. In some embodiments, the antidiabetic agent is chosen from SGLT2 inhibitors, biguanides, sulfonyl ureas, glucosidase inhibitors, PPAR γ agonists, PPAR α/γ dual agonists, aP2 inhibitors, DPP4 inhibitors, insulin sensitizers, glucagon-like peptide-1 (GLP-1) receptor agonists, glucokinase activators, DGAT inhibitors, CCR2 antagonists, 11-s-HSD (hydroxysteroid dehydrogenase), insulin, meglitinides, PTP1B inhibitors, glycogen phosphorylase inhibitors, and glucos-6-phosphatase inhibitors. In some embodiments, the antidiabetic agent is chosen from biguanides and DPP4 inhibitors.

In some embodiments, the antidiabetic agent is chosen from SGLT2 inhibitors. In some embodiments, the SGLT2 inhibitor is chosen from those disclosed in U.S. Pat. No. 6,515,177, PCT/US03/15591, U.S. Ser. No. 11/233,617, US 2006/0194809, US 2006/0063722 A1, PCT/US02/11066, US 2003/0064935, U.S. Pat. No. 6,774,112, US 2005/ 0209166, US 2006/0074031, US 2006/0035841, US 2006/ 0009400, US 2006/0025349, US 2006/0122126, US 2006/ 0019948, US 2006/0194809, WO 03/01180, U.S. Pat. Nos. 6,908,905, 6,815,428, 6,555,519, 6,683,056, EP 598359 A1 (JP 035988 and U.S. Pat. No. 5,731,292), EP 0850948 A1 (U.S. Pat. No. 6,048,842), JP 09188625 A, JP 09124685 A, JP 09124684, EP 773226 A1 (U.S. Pat. No. 5,767,094), JP 08027006 A, EP 684254 A1, JP 10245391 (Dainippon), US 2005/0233982 (Boehringer Ingelheim Corp.), US 2005/ 0119192 (Kissei Pharmaceutical Co.), WO 2006/035796 (Kissei Pharmaceutical Co.), JP 2006/117651 (Taisho Pharmaceutical Co.), JP 2004/4359630 (Yamanouchi Pharmaceutical Co.), WO 2006/080421 (Chugai Seiyaku Kabushiki Kaishi), US 2005/0233988 (Tanabe Seiyaku Co.), WO 2005/ 012321 (Tanabe Seiyaku Co.), U.S. Pat. No. 7,015,201 (Ajinomoto Co.), WO 2006/058597 (Merck Patent GmbH), WO 2006/011469 (Chugai Seiyaku Kabushiki Kaisha), US 2003/0195235 (Johnson & Johnson), and WO 2006/037537 (Boehringer Ingelheim).

In some embodiments, the SGLT2 inhibitor is chosen from those disclosed in Tsujihara, K. et al., Chem. Pharm. Bull., 44:1174-1180 (1996); Hongu, M. et al., Chem. Pharm. Bull., 46:22-33 (1998); Hongu, M. et al., Chem. Pharm. Bull., 46:1545-1555 (1998); and Oku, A. et al., Diabetes, 48:1794-1800 (1999).

In some embodiments, the antidiabetic agent is chosen from biguanides. In some embodiments, the biguanide is metformin or pharmaceutically acceptable salts thereof. In some embodiments, the biguanide is metformin HCl. In some embodiments, the biguanide is phenformin.

In some embodiments, the antidiabetic agent is chosen from sulfonylureas. In some embodiments, the sulfonylurea is chosen from glyburide, glimepiride, glipizide, gliclazide, and chlorpropamide. In some embodiments, the sulfonylurea is glyburide. In some embodiments, the sulfonylurea is glipizide.

In some embodiments, the antidiabetic agent is chosen from glucosidase inhibitors. In some embodiments, the glucosidase inhibitor is chosen from acarbose and miglitol.

In some embodiments, the antidiabetic agent is chosen from PPAR γ agonists. In some embodiments, the PPAR γ agonist is chosen from thiazolidinediones. In some embodiments, the thiazolidinedione is chosen from troglitazone (Warner-Lambert's REZULIN®, disclosed in U.S. Pat. No. 4,572,912), rosiglitazone (SKB), pioglitazone (Takeda), Mitsubishi's MCC-555 (disclosed in U.S. Pat. No. 5,594, 016), Glaxo-Wellcome's GL-262570, englitazone (CP-68722, Pfizer) or darglitazone (CP-86325, Pfizer), isaglitazone (MIT/J&J), JT1-501 (JPNT/P&U), L-895645 (Merck), R-119702 (Sankyo/WL), N,N-2344 (Dr. Reddy/NN), or YM-440 (Yamanouchi).

In some embodiments, the thiazolidinedione is chosen from pioglitazone and rosiglitazone. In some embodiments, the thiazolidinedione is pioglitazone. In some embodiments, the thiazolidinedione is rosiglitazone.

In some embodiments, the antidiabetic agent is chosen from PPAR α/γ dual agonists. In some embodiments, the PPAR α/γ dual agonist is chosen from AR-H039242 (Astra/ Zeneca), GW-409544 (Glaxo-Wellcome), KRP297 (Kyorin Merck) as well as those disclosed by Murakami et al., "A Novel Insulin Sensitizer Acts As a Coligand for Peroxisome Proliferation-Activated Receptor Alpha (PPAR alpha) and PPAR gamma. Effect on PPAR alpha Activation on Abnormal Lipid Metabolism in Liver of Zucker Fatty Rats", Diabetes, 47:1841-1847 (1998), and in U.S. Pat. No. 6,414, 002.

In some embodiments, the antidiabetic agent is chosen from aP2 inhibitors. In some embodiments, the aP2 inhibitor is chosen from those disclosed in U.S. Pat. No. 6,548,529.

In some embodiments, the antidiabetic agent is chosen from DPP4 inhibitors. In some embodiments, the DPP4 inhibitor is chosen from those disclosed in U.S. Pat. No. 6,395,767, WO 99/38501, WO 99/46272, WO 99/67279 (PROBIODRUG), WO 99/67278 (PROBIODRUG), WO 99/61431 (PROBIODRUG), NVP-DPP728A (1-[[[2-[(5-cyanopyridin-2-yl)amino]ethyl]amino]acetyl]-2-cyano-(S)-pyrrolidine) (Novartis) as disclosed by Hughes et al., Biochemistry, 38 (36):11597-11603 (1999), TSL-225 (tryptophyl-1,2,3,4-tetrahydroisoquinoline-3-carboxylic acid (disclosed by Yamada et al., Bioorg. & Med. Chem. Lett., 8:1537-1540 (1998); 2-cyanopyrrolidides and 4-cyanopyrrolidides as disclosed by Ashworth et al, Bioorg. & Med. Chem. Lett., 6 (22):1163-1166 and 2745-2748 (1996).

In some embodiments, the DPP4 inhibitor is chosen from saxagliptin, vildagliptin, linagliptin, alogliptin, and sitagliptin. In some embodiments, the DPP4 inhibitor is chosen from saxagliptin and pharmaceutically acceptable salts thereof. In some embodiments, the DPP4 inhibitor is saxagliptin. In some embodiments, the DPP4 inhibitor is saxagliptin HCl.

In some embodiments, the antidiabetic agent is chosen from meglitinides. In some embodiments, the meglitinide is chosen from repaglinide, nateglinide (Novartis), and KAD1229 (PF/Kissei). In some embodiments, the meglitinide is repaglinide.

In some embodiments, the antidiabetic agent is chosen from glucokinase activators and/or DGAT-1 inhibitors. In some embodiments, the glucokinase activator is chosen from those disclosed in WO 2008/005964. In some embodiments, the DGAT-1 inhibitor is chosen from those disclosed in US2008/0090876A1.

In some embodiments, the antidiabetic agent is chosen from insulin and GLP-1 receptor agonists. In some embodiments, the antidiabetic agent is insulin.

In some embodiments, the antidiabetic agent is chosen from metformin, phenformin, glyburide, glimepiride, glipyride, glipizide, exenatide, chlorpropamide, gliclazide, saxagliptin, sitagliptin, vildagliptin, acarbose, miglitol, troglitazone, pioglitazone, rosiglitazone, pioglitazone, MCC-555, insulin, GL-262570, isaglitazone, englitazone, darglitazone, JTT-501, N,N-2344, L895645, YM-440, R-119702, N,N-2344, YM-440, AJ9677, repaglinide, nateglinide, KAD1129, AR-H039242, GW-409544, KRP297, AC2993, LY315902, and NVP-DPP-728A.

In some embodiments, the at least one other therapeutic agent is chosen from anti-obesity agents. In some embodiments, the anti-obesity agent is chosen from beta 3 adrenergic agonists, lipase inhibitors, serotonin (and dopamine) reuptake inhibitors, thyroid receptor beta modulator, MCH-1 receptor antagonists, agonists of the 5-HT2c receptor, anorectic agents, Neuropeptide Y (NPY) antagonists, Leptin analogs, MC4 receptor agonists, and antagonists of the cannabinoid receptor.

In some embodiments, the beta 3 adrenergic agonist is chosen from AJ9677 (Takeda/Dainippon), SB-418790, L750355 (Merck), CP331648 (Pfizer), and other known beta 3 agonists as disclosed in U.S. Pat. Nos. 5,541,204, 5,770,615, 5,491,134, 5,776,983 and 5,488,064. In some embodiments, the beta 3 adrenergic agonist is chosen from AJ9677, L750355, and CP331648.

In some embodiments, the lipase inhibitor is chosen from orlistat and ATL-962 (Alizyme). In some embodiments, the lipase inhibitor is orlistat.

In some embodiments, the serotonin (and dopamine) reuptake inhibitor is chosen from topiramate (Johnson & Johnson), AXOKINE® (Regeneron), and tetrahydrolipostatin. In some embodiments, the serotonin (and dopamine) reuptake inhibitor is topiramate.

In some embodiments, the thyroid receptor beta modulator is chosen from thyroid receptor ligands as disclosed in WO 97/21993 (U. Cal SF), WO 99/00353 (KaroBio) and WO 00/039077 (KaroBio). In some embodiments, the thyroid receptor beta modulator is chosen from compounds disclosed in WO 99/00353 and WO 00/039077.

In some embodiments, the anorectic agent is chosen from phenylpropanolamine and mazindol.

In some embodiments, the at least one other therapeutic agent is chosen from anti-hyperlipidemic agents. In some embodiments, the hyperlipidemic agent is chosen from HMG CoA reductase inhibitors. In some embodiments, the HMG-CoA reductase inhibitor is chosen from mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171, and rosuvastatin and related statin compounds disclosed in U.S. Pat. No. 5,753,675.

In some embodiments, the HMG-CoA reductase inhibitor is chosen from pyrazole analogs of mevalonolactone derivatives as disclosed in U.S. Pat. No. 4,613,610, indene analogs of mevalonolactone derivatives as disclosed in PCT application WO 86/03488, 6-[2-(substituted-pyrrol-1-yl)-alkyl) pyran-2-ones and derivatives thereof as disclosed in U.S. Pat. No. 4,647,576, Searle's SC-45355 (a 3-substituted pentanedioic acid derivative) dichloroacetate, imidazole analogs of mevalonolactone as disclosed in PCT application WO 86/07054, 3-carboxy-2-hydroxy-propane-phosphonic acid derivatives as disclosed in French Patent No. 2,596,393, 2,3-disubstituted pyrrole, furan and thiophene derivatives as disclosed in European Patent Application No. 0221025, naphthyl analogs of mevalonolactone as disclosed in U.S. Pat. No. 4,686,237, octahydronaphthalenes such as disclosed in U.S. Pat. No. 4,499,289, keto analogs of mevinolin (lovastatin) as disclosed in European Patent Application No. 0142146A2, and quinoline and pyridine derivatives disclosed in U.S. Pat. Nos. 5,506,219 and 5,691,322, and phosphinic acid compounds disclosed in GB 2205837.

In some embodiments, the HMG-CoA reductase inhibitor is chosen from mevastatin, lovastatin (mevinolin), pravastatin, simvastatin, fluvastatin, cerivastatin, atorvastatin, pitavastatin, nisvastatin, itavastatin, and rosuvastatin.

In some embodiments, the at least one other therapeutic agent is chosen from anti-hypertensive agents. In some embodiments, the anti-hypertensive agent is chosen from beta adrenergic blockers, calcium channel blockers (L-type and/or T-type, diuretics, renin inhibitors, ACE inhibitors, AT-1 receptor antagonists, ET receptor antagonists such as disclosed in U.S. Pat. Nos. 5,612,359 and 6,043,265, Dual ET/AII antagonist such as disclosed in WO 00/01389, neutral endopeptidase (NEP) inhibitors, vasopepsidase inhibitors, and nitrates.

In some embodiments, the anti-hypertensive agent is chosen from bisoprolol, carvedilol, metaprolol succinate, diltiazem, verapamil, nifedipine, amlodipine, mibefradil, chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone, torsemide, indapamide, metolazone, triamterene, eplerenone, captopril, zofenopril, fosinopril, enalapril, ceranopril, cilazopril, delapril, pentopril, quinapril, ramipril, lisinopril, perindopril, trandolapril, losartan, irbesartan, valsartan, candesartan, sitaxsentan, atrsentan, omapatrilat, gemopatrilat, hydralazine, isosorbide dinitrate, nitroglycerin, and nitroprusside.

In some embodiments, the at least one other therapeutic agent is chosen from anti-platelet agents. In some embodiments, the anti-platelet agent is chosen from clopidogrel, ticlopidine, prasugrel, and aspirin.

In some embodiments, the at least one other therapeutic agent is chosen from antithrombotic agents and anticoagulant agents. In some embodiments, the antithrombotic agent and/or anticoagulant agent is chosen from thrombin inhibitors, platelet aggregation inhibitors, PAI-1 inhibitors, inhibitors of α-2-antiplasmin, thromboxane receptor antagonists, prostacyclin mimetics, and phosphodiesterase (PDE) inhibitors.

In some embodiments, the antithrombotic agent and/or anticoagulant agent is chosen from clopidogrel, ticlopidine, prasugrel (Eli Lilly), XR-330, T-686, anti-α-2-antiplasmin antibody, ifetroban, dipyridamole, cilostazol, aspirin, ifetroban, picotamide, and ketanserin.

In some embodiments, the at least one other therapeutic agent is chosen from HMG CoA reductase inhibitors, squalene synthetase inhibitors, fibric acid derivatives, aspirin, bile acid sequestrants, ACAT inhibitors, upregulators of LDL receptor activity, cholesterol absorption inhibitors, cholesteryl transfer protein (CETP) inhibitors, ileal Na+/bile acid cotransporter inhibitors, phytoestrogen, beta-lactam cholesterol absorption inhibitors, HDL upregulators, PPAR α-agonists, FXR agonists, LDL catabolism promoters, LDL-receptor inducers, steroidal glycosides, anti-oxidants, anti-homocysteine agents, isoniazids, HMG-CoA synthase inhibitors, lanosterol demethylase inhibitors, PPAR S agonists, sterol regulating element binding protein-I (SREBP-1), beta adrenergic blockers, calcium channel blockers (L-type and/or T-type), diuretics, renin inhibitors, ACE inhibitors, AT-1 receptor antagonists, ET receptor antagonists, dual ET/AII antagonists, neutral endopeptidase (NEP) inhibitors, vasopeptidase inhibitors (dual NEP-ACE inhibitors), and nitrates.

In some embodiments, the at least one other therapeutic agent is chosen from squalene synthetase inhibitors. In some embodiments, the squalene synthetase inhibitor is chosen from α-phosphono-sulfonates disclosed in U.S. Pat. No. 5,712,396, those disclosed by Biller et al., J. Med. Chem., 31:1869-1871 (1998) including isoprenoid (phosphinylmethyl)phosphonates as well as other known squalene synthetase inhibitors, for example, as disclosed in U.S. Pat. Nos. 4,871,721 and 4,924,024 and in Biller, S. A. et al., Current Pharmaceutical Design, 2:1-40 (1996).

In some embodiments, the squalene synthetase inhibitor is chosen from terpenoid pyrophosphates disclosed by Ortiz de Montellano, P. et al., J. Med. Chem., 20:243-249 (1977), the farnesyl diphosphate analog A and presqualene pyrophosphate (PSQ-PP) analogs as disclosed by Corey et al., J. Am. Chem. Soc., 98:1291-1293 (1976), phosphinylphosphonates reported by McClard, R. W. et al., J. Am. Chem. Soc., 109:5544 (1987) and cyclopropanes reported by Capson, T. L., Ph. D. dissertation, June, 1987, Dept. Med. Chem. U of Utah, Abstract, Table of Contents, pp. 16, 17, 40-43, 48-51, Summary.

In some embodiments, the at least one other therapeutic agent is chosen from fibric acid derivatives. In some embodiments, the fibric acid derivative is chosen from those disclosed in U.S. Pat. No. 3,674,836, bile acid sequestrants, poly(diallylmethylamine) derivatives such as disclosed in U.S. Pat. No. 4,759,923, quaternary amine poly(diallyldimethylammonium chloride) and ionenes such as disclosed in U.S. Pat. No. 4,027,009.

In some embodiments, the fibric acid derivative is chosen from fenofibrate, gemfibrozil, clofibrate, bezafibrate, ciprofibrate, clinofibrate, probucol, cholestyramine, colestipol, DEAE-Sephadex (SECHOLEX®, Policexide), cholestagel (Sankyo/Geltex), LIPOSTABIL® (Rhone-Poulenc), EISAI® E-5050 (an N-substituted ethanolamine derivative), imanixil (HOE-402), tetrahydrolipstatin (THL), istigmastanylphosphorylcholine (SPC, Roche), aminocyclodextrin (Tanabe Seiyoku), Ajinomoto A J-814 (azulene derivative), melinamide (Sumitomo), Sandoz 58-035, American Cyanamid CL-277,082 and CL-283,546 (disubstituted urea derivatives), nicotinic acid (niacin), acipimox, acifran, neomycin, p-aminosalicylic acid, aspirin. In some embodiments the fibric acid derivative is chosen from probucol and gemfibrozil.

In some embodiments, the at least one other therapeutic agent is chosen from acyl-CoA: cholesterol O-acyl transferase (ACAT) inhibitors. In some embodiments, the ACAT inhibitor is chosen from those disclosed in Drugs of the Future, 24:9-15 (1999) (Avasimibe); Nicolosi et al., "The ACAT inhibitor, Cl-1011 is effective in the prevention and regression of aortic fatty streak area in hamsters", Atherosclerosis (Shannon, Irel.), 137 (1):77-85 (1998); Ghiselli, G., "The pharmacological profile of FCE 27677: a novel ACAT inhibitor with potent hypolipidemic activity mediated by selective suppression of the hepatic secretion of ApoB100-containing lipoprotein", Cardiovasc. Drug Rev., 16 (1):16-30 (1998); Smith, C. et al., "RP 73163: a bioavailable alkylsulfinyl-diphenylimidazole ACAT inhibitor", Bioorg. Med. Chem. Lett., 6 (1):47-50 (1996); Krause, B. R. et al., Chapter 6: "ACAT Inhibitors: Physiologic Mechanisms for Hypolipidemic and Anti-Atherosclerotic Activities in Experimental Animals", Inflammation: Mediators and Pathways, CRC Press, Inc., publ., Ruffolo, Jr., R. R. et al., eds., pp. 173-198 (1995); Sliskovic et al., "ACAT inhibitors: potential anti-atherosclerotic agents", Curr. Med. Chem., 1 (3):204-225 (1994); Stout et al., "Inhibitors of acyl-CoA: cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)-methyl] ureas with enhanced hypocholesterolemic activity", Chemtracts: Org. Chem., 8 (6):359-362 (1995), or TS-962 (Taisho Pharmaceutical Co. Ltd), as well as F-1394, CS-505, F-12511, HL-004, K-10085 and YIC-C8-434.

In some embodiments, the at least one other therapeutic agent is chosen from upregulators of LDL receptor. In some embodiments, the upregulators of LDL receptor is chosen from MD-700 (Taisho Pharmaceutical Co. Ltd) and LY295427 (Eli Lilly).

In some embodiments, the at least one other therapeutic agent is chosen from cholesterol absorption inhibitors. In some embodiments, the cholesterol absorption inhibitor is chosen from Schering-Plough's SCH48461 (ezetimibe) as well as those disclosed in Atherosclerosis, 115:45-63 (1995) and J. Med. Chem., 41:973 (1998).

In some embodiments, the at least one other therapeutic agent is chosen from cholesteryl transfer protein inhibitors (CETP). In some embodiments, the cholesteryl transfer protein inhibitor (CETP) is chosen from Pfizer's CP-529, 414 as well as those disclosed in WO/0038722 and in EP 818448 (Bayer) and EP 992496, and Pharmacia's SC-744 and SC-795, as well as CETi-1 and JTT-705.

In some embodiments, the at least one other therapeutic agent is chosen from phytoestrogen compounds. In some embodiments, the phytoestrogen compound is chosen from those disclosed in WO 00/30665 including isolated soy bean protein, soy protein concentrate or soy flour as well as an isoflavone such as genistein, daidzein, glycitein or equol, or phytosterols, phytostanol or tocotrienol as disclosed in WO 2000/015201.

In some embodiments, the at least one other therapeutic agent is chosen from beta-lactam cholesterol absorption inhibitors. In some embodiments, the beta-lactam cholesterol absorption inhibitor is chosen from those disclosed in EP 675714.

In some embodiments, the at least one other therapeutic agent is chosen from HDL upregulators. In some embodiments, the HDL upregulator is chosen from LXR agonists.

In some embodiments, the at least one other therapeutic agent is chosen from PPAR α-agonists and FXR agonists.

In some embodiments, the at least one other therapeutic agent is chosen from LDL catabolism promoters. In some embodiments, the LDL catabolism promoters are chosen from those disclosed in EP 1022272.

In some embodiments, the at least one other therapeutic agent is chosen from sodium-proton exchange inhibitors. In some embodiments, the sodium-proton exchange inhibitors are chosen from those disclosed in DE 19622222.

In some embodiments, the at least one other therapeutic agent is chosen from LDL-receptor inducers and steroidal glycosides. In some embodiments, the LDL-receptor inducers and steroidal glycosides are chosen from those disclosed in U.S. Pat. No. 5,698,527 and GB 2304106.

In some embodiments, the at least one other therapeutic agent is chosen from anti-oxidants. In some embodiments, the anti-oxidant is chosen from beta-carotene, ascorbic acid, α-tocopherol, retinol, and Vitamin C.

In some embodiments, the at least one other therapeutic agent is chosen from antihomocysteine agents. In some embodiments, the antihomocysteine agent is chosen from folic acid, a folate, Vitamin B6, Vitamin B12, Vitamin E, and isoniazid.

In some embodiments, the at least one other therapeutic agent is chosen from lanosterol demethylase inhibitors. In some embodiments, the lanosterol demethylase inhibitor is chosen from those disclosed in WO 97/48701.

In some embodiments, the at least one other therapeutic agent is chosen from PPAR δ agonist.

In some embodiments, the at least one other therapeutic agent is chosen from sterol regulating element binding protein-I (SREBP-1). In some embodiments, the SREBP-1 is chosen from those disclosed in WO 2000/050574, sphingolipid, and neutral sphingomyelenase (N-SMase) and fragment thereof. In some embodiments, the SREBP-1 is ceramide.

In some embodiments the at least one other therapeutic agent is chosen from pravastatin, lovastatin, simvastatin, atorvastatin, fluvastatin, pitavastatin, rosuvastatin, ezetimibe, niacin, and cholestagel.

In some embodiments, the method comprises administering to a patient in need thereof a pharmaceutical composition comprising a therapeutically effective amount of (1) at least one compound chosen from compounds of Formula (I) and prodrugs thereof and (2) at least one biguanide and/or at least one DPP4 inhibitor.

In some embodiments, the method comprises administering to a patient in need thereof a pharmaceutical composition comprising a therapeutically effective amount of at least one compound chosen from compounds of Formula (I) and prodrugs thereof alone or in combination with at least one biguanide and/or at least one DPP4 inhibitor.

In some embodiments, the method comprises administering to a patient in need thereof a pharmaceutical composition comprising a therapeutically effective amount of (1) at least one compound chosen from compounds of Formula (I) and prodrugs thereof and (2) metformin.

In some embodiments, the method comprises administering to a patient in need thereof a pharmaceutical composition comprising a therapeutically effective amount of at least one compound chosen from compounds of Formula (I) and prodrugs thereof alone or in combination with metformin.

In some embodiments, the method comprises administering to a patient in need thereof a pharmaceutical composition comprising a therapeutically effective amount of (1) at least one compound chosen from compounds of Formula (I) and prodrugs thereof and (2) saxagliptin.

In some embodiments, the method comprises administering to a patient in need thereof a pharmaceutical composition comprising a therapeutically effective amount of at least one compound chosen from compounds of Formula (I) and prodrugs thereof alone or in combination with saxagliptin.

In some embodiments, the method comprises administering to a patient in need thereof a pharmaceutical composition comprising a therapeutically effective amount of (1) at least one compound chosen from compounds of Formula (I) and prodrugs thereof, and (2) metformin, and (3) saxagliptin.

In some embodiments, the method comprises administering to a patient in need thereof a pharmaceutical composition comprising a therapeutically effective amount of at least one compound chosen from compounds of Formula (I) and prodrugs thereof alone or in combination with metformin and saxagliptin.

In some embodiments, the at least one disease, disorder, and/or condition associated with HFpEF is chosen from skeletal muscle dysfunction, vascular dysfunction, hypertension, pulmonary hypertension, renal failure, anemia, atrial fibrillation, and major adverse cardiovascular events.

In some embodiments, the major adverse cardiovascular event is chosen from myocardial infarction, stroke, cardiovascular death, and cardiovascular hospitalization. In some embodiments, the cardiovascular hospitalization is related to unstable or stable angina pectoris, heart failure, and/or coronary revascularization.

In some embodiments, the method improves cardiac diastolic function. In some embodiments, the method improves cardiac diastolic function compared to placebo. In some embodiments, the method improves cardiac diastolic function compared to placebo when added to standard of care. In some embodiments, the method reduces cardiac fibrosis. In some embodiments, the method reduces cardiac fibrosis compared to placebo. In some embodiments, the method reduces cardiac fibrosis compared to placebo when added to standard of care. In some embodiments, the method reduces hypertrophy. In some embodiments, the method reduces hypertrophy compared to placebo. In some embodiments, the method reduces hypertrophy compared to placebo when added to standard of care.

In some embodiments, the patient is a diabetic patient. In some embodiments, the patient is a non-diabetic patient. In some embodiments, the patient has Hemoglobin A1c (HbA1c)>11%. In some embodiments, the patient has HbA1c in the range of 7.0 to 11%. In some embodiments, the patient has HbA1c of <7.0%. In some embodiments, the patient has HbA1c of <6.5%. In some embodiments, the patient has HbA1c of <6%. In some embodiments, the patient has HbA1c of <5.7%. In some embodiments, the patient has HbA1c in range of 6.0 to 6.9%. In some embodiments, the patient has HbA1c of 5.7 to 6.5%.

In some embodiments, the patient is a male. In some embodiments, the patient is a female. In some embodiments, the patient is ≥40 years old.

In some embodiments, the patient has documented diagnosis of symptomatic heart failure (New York Heart Association, or NYHA, class II-IV) prior to treatment with the compounds, composition, and methods disclosed herein. In some embodiments, the patient has a medical history of symptoms and/or signs of heart failure ≥6 weeks with at least intermittent need for diuretic treatment prior to treatment with the compounds, composition, and methods disclosed herein.

In some embodiments, at least one symptom and/or sign of heart failure is chosen from breathlessness, orthopnoea, paroxysmal nocturnal dyspnoea, reduced exercise tolerance, fatigue, tiredness, increased time to recover after exercise, ankle swelling, elevated jugular venous pressure, hepatojugular reflex, third heart sound (gallop rhythm), laterally displaced apical impulse, weight gain (>2 kg/week), weight loss (in advanced HF), tissue wasting (cachexia), reduced appetite, cardiac murmur, peripheral oedema (ankle, sacral, scrotal), pulmonary crepitations, reduced air entry and dullness to percussion at lung bases (pleural effusion), tachycardia, irregular pulse, tachypnoea, cheyne stokes respiration, hepatomegaly, ascites, cold extremities, oliguria, and/or narrow pulse pressure.

In some embodiments, the patient has left ventricular ejection fraction of ≥45%. In some embodiments, the patient has left ventricular ejection fraction of ≥50%. In some embodiments, the patient has left ventricular ejection fraction within the range of from about 40 to about 49%.

In some embodiments, the evidence of structural heart disease comprises left ventricular hypertrophy and/or left atrial enlargement. In some embodiments, left ventricular hypertrophy is defined by septal thickness or posterior wall thickness ≥1.1 cm. In some embodiments, left atrial enlargement is defined by left atrial width (diameter) ≥3.8 cm, left atrial length ≥5.0 cm, left atrial area ≥20 cm$^2$, left atrial volume ≥55 mL, and/or left atrial volume index ≥29 mL/m$^2$.

In some embodiments, the evidence of structural heart disease is documented by echocardiogram and/or cardiac magnetic resonance imaging within 12 months prior to treatment with the compounds, composition, and methods disclosed herein.

In some embodiments, the patient has NT-proBNP of ≥300 pg/ml without ongoing atrial fibrillation/flutter prior to treatment with the compounds, composition, and methods disclosed herein. In some embodiments, the patient has NT-proBNP of ≥600 pg/ml with ongoing atrial fibrillation/flutter prior to treatment with the compounds, composition, and methods disclosed herein.

In some embodiments, the patient has not received intravenous heart failure therapy, including diuretics, for at least 12 hours prior to treatment with the compounds, composition, and methods disclosed herein. In some embodiments, the patient has not received intravenous heart failure therapy, including diuretics, for at least 24 hours prior to treatment with the compounds, composition, and methods disclosed herein.

In some embodiments, the patient has not received therapy with an SGLT2 inhibitor within 4 weeks prior to treatment with the compounds, composition, and methods disclosed herein.

In some embodiments, the patient does not have type 1 diabetes mellitus.

In some embodiments, the patient does not have eGFR<25 mL/min/1.73 m$^2$ (CKD-EPI formula) (see Levey A S, Stevens L A, Schmid C H, Zhang Y L, Castro A F 3rd, Feldman H I et al. A new equation to estimate glomerular filtration rate. Ann Intern Med. 2009 May 5; 150(9):604-12).

In some embodiments, the patient does not have systolic blood pressure (BP)<95 mmHg on 2 consecutive measurements at 5-minute intervals prior to treatment with the compounds, composition, and methods disclosed herein.

In some embodiments, the patient does not have systolic BP≥160 mmHg if not on treatment with 3 blood pressure lowering medications or ≥180 mmHg irrespective of treatments, on 2 consecutive measurements at 5-minute intervals prior to treatment with the compounds, composition, and methods disclosed herein.

In some embodiments, the patient has not had a myocardial infarction (MI), unstable angina (UA), coronary revascularization (percutaneous coronary intervention (PCI) or coronary artery bypass grafting (CABG)), ablation of atrial flutter/fibrillation, or valve repair/replacement within 12 weeks prior to treatment with the compounds, composition, and methods disclosed herein.

In some embodiments, the patient does not have planned coronary revascularization, ablation of atrial flutter/fibrillation or valve repair/replacement.

In some embodiments, the patient has not had a stroke or transient ischemic attack (TIA) within 12 weeks prior to treatment with the compounds, composition, and methods disclosed herein.

In some embodiments, the patient does not have probable alternative or concomitant diagnoses which in the opinion of the treating physician could account for the patient's HF symptoms and signs (e.g. anaemia, hypothyroidism).

In some embodiments, the patient does not have a body mass index >50 kg/m$^2$.

In some embodiments, the patient does not have primary pulmonary hypertension, chronic pulmonary embolism, severe pulmonary disease including COPD (i.e., requiring home oxygen, chronic nebulizer therapy or chronic oral steroid therapy, or hospitalization for exacerbation of COPD requiring ventilatory assist within 12 months prior to treatment with the compounds, composition, and methods disclosed herein).

In some embodiments, the patient has not had previous cardiac transplantation or complex congenital heart disease, and does not have planned cardiac resynchronization therapy.

In some embodiments, the patient does not have HF due to known infiltrative cardiomyopathy (e.g. amyloid, sarcoid, lymphoma, endomyocardial fibrosis), active myocarditis, constrictive pericarditis, cardiac tamponade, known genetic hypertrophic cardiomyopathy or obstructive hypertrophic cardiomyopathy, arrhythmogenic right ventricular cardiomyopathy/dysplasia (ARVC/D), or uncorrected primary valvular disease.

In some embodiments, the patient does not have a life expectancy of less than 2 years due to any non-cardiovascular condition, based on the treating physician's clinical judgement.

In some embodiments, the patient does not have active malignancy requiring treatment (with the exception of basal cell or squamous cell carcinomas of the skin).

In some embodiments, the patient does not have acute or chronic liver disease with severe impairment of liver function (e.g., ascites, oesophageal varices, coagulopathy).

In some embodiments, the method reduces the time to first occurrence of CV death compared to placebo. In some embodiments, the method reduces the time to first occurrence of CV death compared to placebo when added to standard of care. In some embodiments, the method reduces the time to first occurrence of hospitalization for HF compared to placebo. In some embodiments, the method reduces the time to first occurrence of hospitalization for HF compared to placebo when added to standard of care. In some embodiments, the method reduces the time to first occurrence of an urgent HF visit compared to placebo. In some embodiments, the method reduces the time to first occurrence of an urgent HF visit compared to placebo when added to standard of care. In some embodiments, the urgent HF visit is an emergency department visit and/or an outpatient visit. In some embodiments, the time to first occurrence of CV death is measured at day 30 (±7), 120 (±7), 240 (±7), 360 (±7), 480 (±14), and/or 600 (±14). In some embodiments, the time to first occurrence of hospitalization for HF is measured at day 30 (±7), 120 (±7), 240 (±7), 360 (±7), 480 (±14), and/or 600 (±14). In some embodiments, the time to first occurrence of an urgent HF visit is measured at day 30 (±7), 120 (±7), 240 (±7), 360 (±7), 480 (±14), and/or 600 (±14).

In some embodiments, the method reduces the total number of hospitalizations for HF and CV death compared to placebo. In some embodiments, the method reduces the total number of hospitalizations for HF and CV death compared to placebo when added to standard of care. In some embodiments, the total number of hospitalizations is for first and/or recurrent hospitalizations. In some embodiments, the total number of hospitalizations for HF and CV death is measured at day 30 (±7), 120 (±7), 240 (±7), 360 (±7), 480 (±14), and/or 600 (±14).

In some embodiments, the method improves the patient reported outcomes measured by Kansas City Cardiomyopathy Questionnaire (KCCQ) (i.e., increases KCCQ score). In some embodiments, the method improves the patient reported outcomes measured by KCCQ when added to standard of care. In some embodiments, the method improves the patient reported outcomes measured by KCCQ compared to placebo (i.e., causes a greater increase or lesser decrease compared to placebo). In some embodiments, the method improves the patient reported outcomes measured by KCCQ compared to placebo when added to standard of care. In some embodiments, the patient reported outcomes measured by KCCQ is measured at day 30 (±7), 120 (±7), 240 (±7), 360 (±7), 480 (±14), and/or 600 (±14).

In some embodiments, the method improves the total symptom score (TSS) of the KCCQ at 8 months (i.e., increases TSS score). In some embodiments, the method improves the TSS of the KCCQ at 8 months compared to placebo (i.e., causes a greater increase or lesser decrease compared to placebo). In some embodiments, the method improves the TSS of the KCCQ at 8 months compared to placebo when added to standard of care. In some embodiments, the TSS of the KCCQ is measured at day 30 (±7), 120 (±7), 240 (±7), 360 (±7), 480 (±14), and/or 600 (±14).

In some embodiments, the method improves (i.e., decreases) the NYHA class of the patient (e.g. NYHA class III decreases to class II). In some embodiments, the method improves the NYHA class of the patient when added to standard of care. In some embodiments, the method improves the NYHA class of the patient from baseline to 8 months. In some embodiments, the method improves the NYHA class of the patient from baseline to 8 months when added to standard of care. In some embodiments, the method reduces the proportion of patients with worsened NYHA class compared to placebo (i.e., causes a greater decrease or lesser increase compared to placebo). In some embodiments, the method reduces the proportion of patients with worsened NYHA class from baseline compared to placebo when added to standard of care. In some embodiments, the method reduces the proportion of patients with worsened NYHA class from baseline to 8 months compared to placebo. In some embodiments, the method reduces the proportion of patients with worsened NYHA class from baseline to 8 months compared to placebo when added to standard of care. In some embodiments, the NYHA class of the patient is measured at day 30 (±7), 120 (±7), 240 (±7), 360 (±7), 480 (±14), and/or 600 (±14).

In some embodiments, the method reduces the time to the occurrence of death from any cause compared to placebo. In some embodiments, the method reduces the time to the occurrence of death from any cause compared to placebo when added to standard of care. In some embodiments, the method reduces the time to the first occurrence of hospitalization from any cause compared to placebo. In some embodiments, the method reduces the time to the first occurrence of hospitalization from any cause compared to placebo when added to standard of care. In some embodiments, the time to the occurrence of death from any cause is measured at day 30 (±7), 120 (±7), 240 (±7), 360 (±7), 480 (±14), and/or 600 (±14). In some embodiments, the time to the first occurrence of hospitalization from any cause is measured at day 30 (±7), 120 (±7), 240 (±7), 360 (±7). 480 (±14), and/or 600 (±14).

In some embodiments, the method improves the health status of the patient assessed by EuroQol five-dimensional five-level questionnaire (EQ-5D-5L) (i.e., increases EQ-5D-5L score). In some embodiments, the method improves the health status of the patient assessed by EQ-5D-5L when added to standard of care. In some embodiments, the method improves the health status assessed by EQ-5D-5L compared to placebo (i.e., causes a greater increase or lesser decrease compared to placebo). In some embodiments, the method improves the health status assessed by EQ-5D-5L compared to placebo when added to standard of care. In some embodiments, the health status of the patient assessed by EQ-5D-5L is measured at day 30 (±7), 120 (±7), 240 (±7), 360 (±7), 480 (±14), and/or 600 (±14).

In some embodiments, the method improves the health status of the patient assessed by Patient Global Impression of Severity (PGIS) questionnaire (i.e., decreases severity of symptoms). In some embodiments, the method improves the health status of the patient assessed by PGIS questionnaire when added to standard of care. In some embodiments, the method improves the health status assessed by PGIS questionnaire compared to placebo (i.e., causes a greater decrease or lesser increase compared to placebo). In some embodiments, the method improves the health status assessed by PGIS questionnaire compared to placebo when added to standard of care. In some embodiments, the health status of the patient assessed by PGIS questionnaire is measured at day 30 (±7), 120 (±7), 240 (±7), 360 (±7), 480 (±14), and/or 600 (±14).

In some embodiments, the method improves (i.e., reduces) systolic BP of the patient from baseline. In some embodiments, the method improves systolic BP from baseline when added to standard of care. In some embodiments, the method improves the change in systolic BP from baseline compared to placebo (i.e., causes a greater reduction or lesser increase compared to placebo). In some embodiments, the method improves the change in systolic BP from baseline compared to placebo when added to standard of care. In some embodiments, systolic BP of the patient is measured at day 30 (±7), 120 (±7), 240 (±7), 360 (±7), 480 (±14), and/or 600 (±14).

In some embodiments, the method improves (i.e., reduces) the body weight of the patient from baseline. In some embodiments, the method reduces the body weight of the patient from baseline when added to standard of care. In some embodiments, the method improves the change in body weight from baseline compared to placebo (i.e., causes a greater reduction or lesser increase compared to placebo). In some embodiments, the method improves the change in body weight from baseline compared to placebo when added to standard of care. In some embodiments, the body weight of the patient is measured at day 30 (±7), 120 (±7), 240 (±7), 360 (±7), 480 (±14), and/or 600 (±14).

In some embodiments, the method does not reduce eGFR of the patient from baseline. In some embodiments, the method does not reduce eGFR of the patient from baseline when added to standard of care. In some embodiments, the method improves the change in eGFR from baseline compared to placebo (i.e., causes a greater increase or lesser decrease compared to placebo). In some embodiments, the method improves the change in eGFR from baseline compared to placebo when added to standard of care. In some embodiments, eGFR of the patient is measured at day 30 (±7), 120 (±7), 240 (±7), 360 (±7), 480 (±14), and/or 600 (±14).

In some embodiments, the method improves (i.e., increases) the KCCQ clinical summary score (i.e., the sum of the total symptom and physical function scores), overall summary score (i.e., the sum of the total symptom, physical function, social limitations and quality of life scores), TSS, and/or quality of life (QoL) score of the patient. In some embodiments, the method improves the KCCQ clinical summary score, overall summary score, TSS, and/or QoL score of the patient when added to standard of care. In some embodiments, the method improves the KCCQ clinical summary score, overall summary score, TSS, and/or QoL score compared to placebo. In some embodiments, the method improves the KCCQ clinical summary score, overall summary score, TSS, and/or QoL score compared to placebo when added to standard of care. In some embodiments, the KCCQ clinical summary score, overall summary score, TSS, and/or QoL score is measured at day 30 (±7), 120 (±7), 240 (±7), 360 (±7), 480 (±14), and/or 600 (±14).

In some embodiments, the standard of care comprises treatment to control co-morbidities and/or treatments for reducing the composite of CV death and heart failure events. In some embodiments, the heart failure events are chosen from hospitalization for HF and/or urgent HF visits. In some embodiments, the standard of care comprises controlling blood pressure, heart rate, blood volume, and myocardial ischemia. In some embodiments, the standard of care changes during the course of treatment.

All of the publications, patents and published patent applications referred to in this application are specifically incorporated by reference herein.

The terms "treating" or "treatment" or "to treat" refer to therapeutic measures that cure, slow down, lessen symptoms of, and/or halt progression of a diagnosed pathologic disease, disorder, or condition. Treatment need not result in a complete cure of the condition; partial inhibition or reduction of the condition being treated is encompassed by this term.

The terms "preventing" or "prevent" or "to prevent" refer to prophylactic or preventative measures that prevent and/or inhibit, decrease, and/or reduce the likelihood of occurrence of the development of a targeted pathologic disease, disorder, or condition in at least one statistical, biological, and/or clinically significant manner.

The term "about" as used herein refers to within 20%, such as within 10% and further such as within 5%, of a given value or range.

The term "or" is used herein to mean, and is used interchangeably with, the term "and/or," unless context clearly indicates otherwise.

The term "HFpEF" as used herein refers to heart failure with preserved ejection wherein EF>40% and evidence of structural heart disease.

The term "non-diabetic patient" as used herein refers to a patient without documented type 1 or type 2 diabetes prior to treatment with the compounds, compositions, and methods disclosed herein.

The term "other therapeutic agent" as used herein refers to a therapeutic agent other than the at least one compound chosen from compounds of Formula (I) and prodrugs thereof.

The term "prodrug ester" as used herein includes esters and carbonates that may be converted, for example, under physiological conditions or by solvolysis, to dapagliflozin. Thus, the term prodrug ester includes metabolic precursors of dapagliflozin that are pharmaceutically acceptable. The term prodrug ester also includes covalently bonded carriers that release dapagliflozin in vivo when such prodrug is administered to a patient. Non-limiting examples of prodrug esters include esters and carbonates formed by reacting one or more hydroxyls of dapagliflozin with alkyl, alkoxy, or aryl substituted acylating agents employing procedures known to those skilled in the art to generate acetates, pivalates, methylcarbonates, benzoates and the like.

Various forms of prodrugs are known in the art. For examples of such prodrug derivatives, see: (1) Design of Prodrugs, edited by H. Bundgaard, (Elsevier, 1985) and Methods in Enzymology, Vol. 42, p. 309-396, edited by K. Widder, et al. (Academic Press, 1985); (2) A Textbook of Drug Design and Development, edited by Krogsgaard-Larsen and H. Bundgaard, Chapter 5 "Design and Application of Prodrugs", by H. Bundgaard p. 113-191 (1991); (3) H. Bundgaard, Advanced Drug Delivery Reviews, 8, 1-38 (1992); (4) H. Bundgaard, et al., Journal of Pharmaceutical Sciences, 77, 285 (1988); and (5) N. Kakeya, et al., Chem Pharm Bull, 32, 692 (1984).

In some embodiments, the at least one other therapeutic agent is administered before, after, or concurrently with the at least one compound chosen from compounds of Formula (I) and prodrugs thereof. In some embodiments, the at least one other therapeutic agent is administered before the at least one compound chosen from compounds of Formula (I) and prodrugs thereof. In some embodiments, the at least one other therapeutic agent is administered after the at least one compound chosen from compounds of Formula (I) and prodrugs thereof. In some embodiments, the at least one other therapeutic agent is administered concurrently with the at least one compound chosen from compounds of Formula (I) and prodrugs thereof.

The effectiveness of the compounds of the present disclosure in treating and/or preventing HFpEF and/or diseases, disorders, and/or conditions associated therewith can readily be determined by a person of ordinary skill in the relevant art. Determining and adjusting an appropriate dosing regimen (e.g., adjusting the amount of compound per dose and/or number of doses and frequency of dosing) can also readily be performed by a person of ordinary skill in the relevant art. One or any combination of diagnostic methods, including physical examination, assessment and monitoring of clinical symptoms, and performance of analytical tests and methods described herein, may be used for monitoring the health status of the patient.

An effective amount or therapeutically effective amount refers to an amount of at least one compound of the present disclosure or a pharmaceutical composition comprising at least one such compound that, when administered to a patient, either as a single dose or as part of a series of doses, is effective to produce at least one therapeutic effect. Optimal doses may generally be determined using experimental models and/or clinical trials. Design and execution of preclinical and clinical studies for each of the therapeutics (including when administered for prophylactic benefit) described herein are well within the skill of a person of ordinary skill in the relevant art. The optimal dose of a therapeutic may depend upon the body mass, weight, and/or blood volume of the patient. Patients may generally be monitored for therapeutic effectiveness using assays suitable for the disease, disorder and/or condition being treated or prevented, which assays will be familiar to those having ordinary skill in the art and are described herein. The level of a compound that is administered to a patient may be monitored by determining the level of the compound (or a metabolite of the compound) in a biological fluid, for example, in the blood, blood fraction (e.g., serum), and/or in the urine, and/or other biological sample from the patient. Any method practiced in the art to detect the compound, or metabolite thereof, may be used to measure the level of the compound during the course of a therapeutic regimen.

The dose of a compound described herein may depend upon the patient's condition, that is, stage of the disease, severity of symptoms caused by the disease, general health status, as well as age, gender, and weight, and other factors apparent to a person of ordinary skill in the medical art. Similarly, the dose of the therapeutic for treating a disease, disorder, and/or condition may be determined according to parameters understood by a person of ordinary skill in the medical art.

In some embodiments, the at least one compound chosen from compounds of Formula (I) and prodrugs thereof is administered at a dose equivalent of from about 1 to about 1000 mg/day dapagliflozin. In some embodiments, the at least one compound chosen from compounds of Formula (I) and prodrugs thereof is administered at a dose equivalent of from about 0.5 to about 200 mg/day dapagliflozin. In some embodiments, the at least one compound chosen from compounds of Formula (I) and prodrugs thereof is administered at a dose equivalent of from about 2 to about 400 mg/day dapagliflozin. In some embodiments, the at least one compound chosen from compounds of Formula (I) and prodrugs thereof is administered at a dose equivalent of from about 1 to about 100 mg/day dapagliflozin. In some embodiments, the at least one compound chosen from compounds of Formula (I) and prodrugs thereof is administered at a dose equivalent of from about 2.5 to about 75 mg/day dapagliflozin. In some embodiments, the at least one compound chosen from compounds of Formula (I) and prodrugs thereof is administered at a dose equivalent of from about 2.5 to about 50 mg/day dapagliflozin. In some embodiments, the at least one compound chosen from compounds of Formula (I) and prodrugs thereof is administered at a dose equivalent of from about 1 to about 50 mg/day dapagliflozin. In some embodiments, the at least one compound chosen from compounds of Formula (I) and prodrugs thereof is administered at a dose equivalent of from about 1 to about 20 mg/day dapagliflozin. In some embodiments, the at least one compound chosen from compounds of Formula (I) and prodrugs thereof is administered at a dose equivalent of from about 2.5 to about 20 mg/day dapagliflozin. In some embodiments, the at least one compound chosen from compounds of Formula (I) and prodrugs thereof is administered at a dose equivalent of from about 2.5 to about 10 mg/day dapagliflozin. In some embodiments, the at least one compound chosen from compounds of Formula (I) and prodrugs thereof is administered at a dose equivalent of about 10 mg/day dapagliflozin. In some embodiments, the at least one compound chosen from compounds of Formula (I) and prodrugs thereof is administered at a dose equivalent of about 5 mg/day dapagliflozin. In some embodiments, the at least one compound chosen from compounds of Formula (I) and prodrugs thereof is administered at a dose equivalent of about 2.5 mg/day dapagliflozin.

In some embodiments, the pharmaceutical composition comprises the at least one compound chosen from compounds of Formula (I) and prodrugs thereof in a weight ratio to the at least one other therapeutic agent within the range of from about 0.01:1 to about 300:1. In some embodiments, the pharmaceutical composition comprises the at least one compound chosen from compounds of Formula (I) and prodrugs thereof in a weight ratio to the at least one other therapeutic agent within the range of from 0.1:1 to 200:1. In some embodiments, the pharmaceutical composition comprises the at least one compound chosen from compounds of Formula (I) and prodrugs thereof in a weight ratio to the at least one other therapeutic agent within the range of from about 0.2:1 to about 100:1.

In some embodiments, the weight ratio for the combination of the at least one compound chosen from compounds of Formula (I) and prodrugs thereof and the at least one other therapeutic agent is within the range of from about 0.01:1 to about 300:1. In some embodiments, the weight ratio for the combination of the at least one compound chosen from compounds of Formula (I) and prodrugs thereof and the at least one other therapeutic agent is within the range of from about 0.1:1 to about 200:1. In some embodiments, the weight ratio for the combination of the at least one compound chosen from compounds of Formula (I) and prodrugs thereof and the at least one other therapeutic agent is within the range of from about 0.2:1 to about 100:1.

Pharmaceutical compositions may be administered in any manner appropriate to the disease, disorder, and/or condition to be treated as determined by persons of ordinary skill in the medical arts. An appropriate dose and a suitable duration and frequency of administration will be determined by such factors as discussed herein, including the condition of the patient, the type and severity of the patient's disease, the particular form of the active ingredient, and the method of administration. In general, an appropriate dose (or effective dose) and treatment regimen provides the composition(s) as described herein in an amount sufficient to provide therapeutic and/or prophylactic benefit (for example, an improved clinical outcome, such as more frequent complete or partial remissions, or longer disease-free and/or overall survival, or a lessening of symptom severity or other benefit as described in detail above).

The pharmaceutical composition can be formulated employing conventional solid or liquid vehicles, diluents, and pharmaceutical additives as appropriate for the mode of desired administration. The pharmaceutical compositions can be administered by a variety of routes including, for example, orally, in the form of tablets, capsules, granules, powders, and the like, parenterally, in the form of injectable preparations, intranasally, rectally, and transdermally, in the form of patches, for example.

The above dosage forms can also include the necessary physiologically acceptable carrier (i.e., a non-toxic, inert solid, semi-solid or liquid filler, diluent, encapsulating material or formulation auxiliary of any type), excipient, lubricant, buffer, antibacterial, bulking agent (such as mannitol), adjuvant, and the like.

Some examples of materials which can serve as pharmaceutically acceptable carriers are sugars, such as lactose, glucose and sucrose; starches, such as corn starch and potato starch; cellulose and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such a propylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; and phosphate buffer solutions, as well as other non-toxic compatible lubricants, such as sodium lauryl sulfate and magnesium stearate; coloring agents; releasing agents; coating agents; sweetening; flavoring; and perfuming agents; preservatives; and antioxidants.

Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters, such as ethyl oleate. Proper fluidity can be maintained, for example, by the use of a coating such as lecithin, by the maintenance of the required particle size in the case of dispersions, and by the use of surfactants.

Examples of adjuvants include preservative agents, wetting agents, emulsifying agents, dispersing agents, suspending agents, sweetening, flavoring, and perfuming agents. Prevention of the action of microorganisms can be ensured by various antibacterial and antifungal agents, for example, parabens, chlorobutanol, phenol, sorbic acid, and the like. It can also be desirable to include isotonic agents, for example, sugars, sodium chloride and the like. Prolonged absorption of the injectable pharmaceutical form can be brought about by the use of agents delaying absorption, for example, aluminum monostearate and gelatin. Suspending agents include, for example, ethoxylated isostearyl alcohols, polyoxyethylene sorbitol, and sorbitan esters, microcrystalline cellulose, aluminum metahydroxide, bentonite, agar-agar, tragacanth, and mixtures thereof.

The various pharmaceutical compositions employed in the methods of the invention can optionally include one or more fillers or excipients in an amount within the range of from about 0% to about 90% by weight and in some embodiments from about 1% to about 80% by weight. Examples of suitable fillers or excipients include, but are not limited to, lactose, sugar, corn starch, modified corn starch, mannitol, sorbitol, inorganic salts, such as calcium carbonate, and cellulose derivatives, such as wood cellulose and microcrystalline cellulose.

One or more binders can be present in addition to or in lieu of the fillers in an amount within the range of from about 0% to about 35%. In some embodiments, the binders are present in an amount of from about 0.5% to about 30% by weight of the composition. Examples of suitable binders include polyvinylpyrrolidone (molecular weight ranging from about 5000 to about 80,000 and in some embodiments about 40,000), lactose, starches, such as corn starch, modified corn starch, sugars, gum acacia and the like, as well as a wax binder in finely powdered form (less than 500 microns), such as carnauba wax, paraffin, spermaceti, polyethylenes and microcrystalline wax.

In some embodiments, the pharmaceutical composition is in the form of a tablet, wherein the tablet includes one or more tableting lubricants in an amount within the range of from about 0.2% to about 8% by weight of composition. In some embodiments, the tableting lubricant(s) is in an amount within the range of from about 0.5% to about 2% by weight of the composition. Examples of suitable tableting lubricants include, but are not limited to, magnesium stearate, stearic acid, palmitic acid, calcium stearate, talc, carnauba wax, and the like. Other ingredients can optionally be present, including, for example, preservatives, stabilizers, colorants, anti-adherents and silica flow conditioners or glidants, such as Syloid brand silicon dioxide.

In some embodiments, the pharmaceutical composition is in the form of a tablet, wherein the tablet includes a coating layer which can comprise from about 0% to about 15% by weight of the tablet composition. The coating layer can comprise any conventional coating formulations that can include, for example, one or more film-formers or binders and/or one or more plasticizers. Examples of suitable film-formers or binders include, but are not limited to, hydrophilic polymers, such as hydroxypropylmethylcellulose, hydrophobic polymers, such as methacrylic acid esters, neutral polymers, ethyl cellulose, cellulose acetate, polyvinyl alcohol-maleic anhydride copolymers, p-pinene polymers, glyceryl esters of wood resins and the like. Examples of suitable plasticizers include, but are not limited to, triethyl citrate, diethyl phthalate, propylene glycol, glycerin, butyl phthalate, castor oil and the like. Both core tablets as well as coating formulations can contain aluminum lakes to provide color.

In some embodiments, the pharmaceutical composition is in the form of a tablet, wherein film-formers are applied to the tablet from a solvent system containing one or more solvents including water, alcohols such as methyl alcohol, ethyl alcohol and isopropyl alcohol, ketones such as acetone and ethylmethyl ketone, chlorinated hydrocarbons such as methylene chloride, dichloroethane, and 1,1,1-trichloroethane.

In some embodiments, the pharmaceutical composition is in the form of a tablet, wherein color is applied together with the film former, plasticizer, and solvent compositions.

In some embodiments, the pharmaceutical composition for use in the methods of the invention in the form of a tablet can be obtained by a process comprising the steps of:
  a) mixing the inactive ingredients with the at least one compound of Formula (I);
  b) formulating granules;
  c) drying and/or screening the granules;
  d) blending the granules; and
  e) tableting the blend obtained in (d) into tablets.

In some embodiments, step a) of the process employs impact blending or milling and/or sizing equipment. In some embodiments, the granules in step b) of the process are formulated by dry granulation, wet granulation, or direct compression. In some embodiments, the granules are formulated by dry granulation. In some embodiments, the granules in step d) of the process are blended with a tableting aid or a lubricant and filler.

In some embodiments, the pharmaceutical composition in the form of a capsule can be obtained by a process comprising the steps of:
a) mixing the inactive ingredients with the at least one compound of Formula (I) using a combination of blending and milling processes;
b) formulating granules;
c) drying and/or screening the granules; and
d) loading the granules into capsules.

In some embodiments, step a) of the process employs impact milling or blending and/or sizing equipment. In some embodiments, the granules in step b) of the process are formulated by dry granulation, wet granulation, or direct compression. In some embodiments, the granules are formulated by dry granulation.

In some embodiments, the pharmaceutical composition may also contain adjuvants such as preservatives, wetting agents, emulsifying agents, and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents which delay absorption such as aluminum monostearate and gelatin.

In some embodiments, it is desirable to slow the absorption of the drug from subcutaneous or intramuscular injection. In some embodiments, this is accomplished by the use of a liquid suspension of crystalline or amorphous material with poor water solubility. The rate of absorption of the drug then depends upon its rate of dissolution which, in turn, may depend upon crystal size and crystalline form. In some embodiments, delayed absorption is accomplished by dissolving or suspending the drug in an oil vehicle.

In some embodiments, the pharmaceutical composition is in an injectable depot form. In some embodiments, the injectable depot form comprises microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers suitable for use herein include poly (orthoesters) and poly(anhydrides). In some embodiments, depot injectable formulations are prepared by entrapping the drug in liposomes or microemulsions which are compatible with body tissues.

In some embodiments, the pharmaceutical composition is an injectable formulation, wherein the injectable formulation may be sterilized, for example, by filtration through a bacterial-retaining filter or by incorporating sterilizing agents in the form of sterile solid compositions which can be dissolved or dispersed in sterile water or other sterile injectable medium just prior to use.

In some embodiments, the pharmaceutical composition is a solid dosage form suitable for oral administration. Solid dosage forms for oral administration include capsules, tablets, pills, powders and granules. In some embodiments, the at least one compound chosen from compounds of Formula (I) and prodrugs thereof is mixed with at least one inert, pharmaceutically acceptable excipient or carrier, such as sodium citrate or dicalcium phosphate and/or a) fillers or extenders such as starches, lactose, sucrose, glucose, mannitol, and silicic acid; b) binders such as carboxymethylcellulose, alginates, gelatin, polyvinylpyrrolidone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay, and/or i) lubricants such as talc, calcium stearate, magnesium stearate, solid polyethylene glycols, sodium lauryl sulfate, and mixtures thereof. In some embodiments, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

In some embodiments tablets, dragees, capsules, pills, and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

In some embodiments the at least one compound chosen from compounds of Formula (I) and prodrugs thereof may be in micro-encapsulated form, if appropriate, with one or more of the above-mentioned excipients.

In some embodiments the pharmaceutical composition may be in liquid dosage form suitable for oral administration including pharmaceutically acceptable emulsions, solutions, suspensions, syrups, and elixirs. In some embodiments, the liquid dosage form may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols, and fatty acid esters of sorbitan, and mixtures thereof.

The following examples provide illustrative embodiments of the disclosure. One of ordinary skill in the art will recognize the numerous modifications and variations that may be performed without altering the spirit or scope of the disclosure. Such modifications and variations are encompassed within the scope of the disclosure. The examples provided do not in any way limit the disclosure.

EXAMPLE

Example 1

Double-Blind, Randomized Placebo-Controlled
Phase M Study to Evaluate the Effect of
Dapagliflozin on Reducing CV Death or Worsening
Heart Failure in Patients with Heart Failure with
Preserved Ejection Fraction (HFpEF)

Study Design: Overall Design

This is an international, multicenter, parallel-group, event-driven, randomized, double-blind, placebo-controlled study in HFpEF patients, evaluating the effect of dapagliflozin 10 mg versus placebo, given once daily in addition to background regional standard of care therapy, including treatments to control co-morbidities, in reducing the composite of CV death or heart failure events.

Adult patients with HFpEF (defined for the purposes of this study as LVEF>40% and evidence of structural heart disease) aged 240 years and with NYHA class II-IV (see Appendix A) who meet the inclusion criteria, and none of the exclusion criteria, will be randomized in a 1:1 ratio to receive either dapagliflozin 10 mg or placebo. Randomized treatment will be started as soon as possible and within 24 hours after randomization. Patients will be enrolled to reach the target of approximately 4700 randomized patients.

Study closure procedures will be initiated when the predetermined number of primary endpoints are predicted to have occurred (n=844), i.e., the Primary Analysis Censoring Date (PACD). Patients will be scheduled for a Study Closure Visit (SCV) within 6 weeks of the PACD. The study duration, and the number of patients, may be changed if the randomization rate or the event rate is different than anticipated. The study may be terminated early.

Data on baseline characteristics, endpoints and AEs will be collected.

Study Design: Scientific Rationale for Study Design

This is a randomized, multi-center, double-blind, parallel-group study. The target population includes adult (aged 40 years) male and female patients with HFpEF, which is defined in this study as individuals with an established diagnosis of heart failure and a LVEF>40% and structural heart disease who meet natriuretic peptide thresholds. Patients will be out-patients or will be enrolled and randomized during hospitalization for heart failure or within 21 days of discharge from hospitalization for heart failure (subacute subgroup)

The study population will include patients both with and without T2D. Enrollment in the study may be capped based on the proportion of patients with/without T2D, in certain LVEF categories, in each NYHA class, with/without atrial fibrillation, randomized during or early after HF hospitalization (subacute subgroup), and geographic region.

The control group will receive placebo. All patients will be treated according to local guidelines on standard of care treatment for patients with HFpEF, focusing on treatment of HF symptoms (e.g. diuretics) and comorbidities (including treatment for high blood pressure, ischaemic heart disease, atrial fibrillation).

The study population will include patients with eGFR>25 m/min/1.73 m$^2$ (CKD-EPI formula).

The primary efficacy endpoints of the study are adjudicated CV death and HF events (hospitalization for HF or urgent HF visit). Heart failure events include both HF hospitalizations and unplanned HF visits requiring urgent treatment independently of whether the exacerbation of HF results in hospitalization (according to CDISC definitions; Hicks et al., Draft Definitions for CDISC, Aug. 20, 2014; Hicks et al., J Am Coll Cardiol, 71:1021-34 (2018)).

While CV death and HF hospitalisations are important to patients and health-care systems, the impact of HF on patients' symptoms and physical/social functioning may also be important. In order to evaluate the treatment effects on these aspects of the impact of HF, we will use the Kansas City Cardiomyopathy Questionnaire (KCCQ), a disease-specific patient reported outcomes (PRO) measure developed for patients with chronic HF. The KCCQ has shown to be a valid, reliable and responsive measure for patients with HF (Greene at al., JAMA Cardiol., 3(3):252-59 (2018); Spertus et al., J Am Heart, 150(4)707-15 (2005)).

Study Design: Justification for Dose

The 10 mg dose of dapagliflozin has a well-characterized efficacy and safety profile in the T2D clinical development program and is the recommended dose in the majority of countries worldwide.

Study Population

In this protocol, "enrolled" patients are defined as those who sign the informed consent form (ICF) and received E-Code. "Randomized" patients are defined as those who undergo randomization and receive a randomization code.

Patients are eligible to be randomized in the study only if all of the following inclusion criteria and none of the exclusion criteria apply. Enrolled patients who for any reason are not randomized are considered screen failure.

Study Population: Inclusion Criteria

Subjects are eligible to be randomized in the study only if all of the following inclusion criteria and none of the exclusion criteria apply.
1. Provision of signed informed consent prior to any study specific procedures.
2. Male or female patients age ≥240 years.
3. Documented diagnosis of symptomatic heart failure (NYHA class II-IV) at enrollment, and a medical history of typical symptoms/signs of heart failure ≥6 weeks before enrollment with at least intermittent need for diuretic treatment.
4. Left Ventricular Ejection Fraction (LVEF)>40% and evidence of structural heart disease (i.e., left ventricular hypertrophy or left atrial enlargement) documented by the most recent echocardiogram, and/or cardiac MR within the last 12 months prior to enrollment. For patients with prior acute cardiac events or procedures that may reduce LVEF, e.g. as defined in exclusion criterion 6, qualifying cardiac imaging assessment at least 12 weeks following the procedure/event is required.
5. NT-pro BNP≥300 pg/ml at Visit 1 for patients without ongoing atrial fibrillation/flutter. If ongoing atrial fibrillation/flutter at Visit 1, NT-pro BNP must be ≥600 pg/mL.
6. Patients may be ambulatory, or hospitalized; patients must be off intravenous heart failure therapy (including diuretics) for at least 12 hours prior to enrollment and 24 hours prior to randomization.

Study Population: Exclusion Criteria
1. Receiving therapy with an SGLT2 inhibitor within 4 weeks prior to randomization or previous intolerance to an SGLT2 inhibitor
2. Type 1 diabetes mellitus (TiD)
3. eGFR<25 mL/min/1.73 m2 (CKD-EPI formula) at Visit 1
4. Systolic blood pressure (BP)<95 mmHg on 2 consecutive measurements at 5-minute intervals, at Visit 1 or at Visit 2
5. Systolic BP≥160 mmHg if not on treatment with ≥3 blood pressure lowering medications or ≥180 mmHg irrespective of treatments, on 2 consecutive measurements at 5-minute intervals, at Visit 1 or at Visit 2.
6. MI, unstable angina, coronary revascularization (percutaneous coronary intervention (PCI) or coronary artery bypass grafting (CABG)), ablation of atrial flutter/fibrillation, valve repair/replacement within 12 weeks prior to enrollment. Before enrollment, these patients must have their qualifying echocardiography and/or cardiac MRI examination at least 12 weeks after the event.
7. Planned coronary revascularization, ablation of atrial flutter/fibrillation and valve repair/replacement.

8. Stroke or transient ischemic attack (TIA) within 12 weeks prior to enrollment
9. Probable alternative or concomitant diagnoses which in the opinion of the investigator could account for the patient's HF symptoms and signs (e.g. anaemia, hypothyroidism)
10. Body mass index >50 kg/m2
11. Primary pulmonary hypertension, chronic pulmonary embolism, severe pulmonary disease including COPD (i.e., requiring home oxygen, chronic nebulizer therapy or chronic oral steroid therapy, or hospitalization for exacerbation of COPD requiring ventilatory assist within 12 months prior to enrollment)
12. Previous cardiac transplantation, or complex congenital heart disease. Planned cardiac resynchronization therapy.
13. HF due to any of the following: known infiltrative cardiomyopathy (e.g. amyloid, sarcoid, lymphoma, endomyocardial fibrosis), active myocarditis, constrictive pericarditis, cardiac tamponade, known genetic hypertrophic cardiomyopathy or obstructive hypertrophic cardiomyopathy, arrhythmogenic right ventricular cardiomyopathy/dysplasia (ARVC/D), or uncorrected primary valvular disease
14. A life expectancy of less than 2 years due to any non-cardiovascular condition, based on investigator's clinical judgement.
15. Inability of the patient, in the opinion of the investigator, to understand and/or comply with study medications, procedures and/or follow-up OR any conditions that, in the opinion of the investigator, may render the patient unable to complete the study
16. Active malignancy requiring treatment (with the exception of basal cell or squamous cell carcinomas of the skin).
17. Acute or chronic liver disease with severe impairment of liver function (e.g., ascites, oesophageal varices, coagulopathy)
18. Women of child-bearing potential (i.e., those who are not chemically or surgically sterilized or post-menopausal) not willing to use a medically accepted method of contraception considered reliable in the judgment of the investigator OR who have a positive pregnancy test at randomization OR who are breast-feeding
19. Involvement in the planning and/or conduct of the study
20. Previous randomization in the present study
21. Participation in another clinical study with an investigational product (IP) or device during the last month prior to enrollment Study Treatments Study treatment in this study refers to dapagliflozin or matching placebo.

Study Treatments: Treatments Administered

| Study Treatments | | |
| --- | --- | --- |
|  | Dapagliflozin | Placebo |
| Investigational Product name | Dapagliflozin 10 mg | Matching placebo 10 mg |
| Route of administration | Oral | Oral |
| Dosing instructions | Once daily | Once daily |

Study Treatments: Concomitant Therapy—Prohibited Medication

Concomitant treatment with open label SGLT2 inhibitors e.g., dapagliflozin, empagliflozin, canagliflozin, ertugliflozin, tofogliflozin and luseogliflozin and fix dose combinations containing these drugs will not be used.

Study Treatments: Concomitant Therapy—Heart Failure Background Standard of Care

The patients may be on background standard of care therapies for patients with HFpEF according to local guidelines, including diuretics when needed to control symptoms and volume overload and adequate treatment of co-morbidities such as hypertension and ischaemic heart disease.

Study Treatments: Concomitant Therapy—Anti-Diabetes Treatment

Treatment of diabetes may follow established guidelines, such as according to glycaemic goals as recommended by the American Diabetes Association (ADA) and European Association for the Study of Diabetes (EASD) in their joint Position Statement (Inzucchi et al., Diabetes Care, 35(6): 1364-79 (2012); Inzucchi et al., Diabetes Care, 38(1):140-49 (2015)).

If needed, T2D treatments may be adjusted at the discretion of the Investigator or diabetes health care provider.

Study Treatments: Concomitant Therapy—Other Concomitant Treatment

Medications other than described above, which is considered necessary for the patient's safety and wellbeing, may be given at the discretion of the Investigator.

Discontinuation of Treatment

If the patient temporarily or permanently discontinues IP, the patient may remain in the study and study visits and data collection may continue according to the study protocol until study closure.

Patients may be discontinued from IP in the following situations:
  Contraindication to further dosing with IP, in the opinion of the Investigator, such as adverse event or other safety reasons.
  Severe non-compliance with the study protocol.
  Diabetic ketoacidosis (DKA).
  Positive pregnancy test.
  Patient decision.

Study Assessments and Procedures: Enrollment Period (Visit 1, Enrollment (Day −21 to Day −1)

Enrollment of hospitalized patients is allowed.

At enrollment the following assessments and procedures will be completed:
  The patient signs the ICF
    Patients who agree to the optional sampling of blood for genetic research will provide their consent
  The investigator reviews the inclusion and exclusion criteria
  The patient will be enrolled and assigned an E-code in IxRS assuming inclusion/exclusion criteria are met
  Demography and relevant medical history (including prior cardiac imaging assessments) will be recorded
  A physical examination will be conducted
  NYHA Functional Classification will be evaluated and recorded
  12-lead ECG will be recorded
  Vital signs (BP, pulse), height and weight will be assessed and recorded
  Blood samples will be taken for NT-proBNP, creatinine (for calculation of eGFR) and HbA1c assessment (central laboratory)

Study Assessments and Procedures: Treatment Period (Visit 2. Randomization (Day 1))

Prior to Visit 2, the investigator will assess eligibility based on the central laboratory assessments from Visit 1. Patients not eligible will be considered screen failures and should not continue to Visit 2.

Randomisation of hospitalized patients is allowed.

At randomisation, the following assessments and procedures will be completed:
- Medical history (including cardiac imaging assessments) will be re-assessed
- A physical examination will be conducted
- A pregnancy test for women of child-bearing potential will be done locally with a dipstick provided by central laboratory with result recorded in the medical record
- Vital signs (BP, pulse) will be assessed and recorded
- NYHA Functional Classification will be evaluated and recorded
- The investigator will re-assess the inclusion and exclusion criteria
- KCCQ, PGIS and EQ-5D-5L questionnaires will be completed
- Review of concomitant medication and recording of relevant medications
- If the patient has experienced any SAEs since last visit, this will be recorded in the eCRF
- Randomisation 1:1 ratio to IP (either dapagliflozin at 10 mg or placebo) will be done in IxRS
- IP will be dispensed via IxRS to the patient. The patient will be instructed to take the IP in accordance with protocol without interruptions, and to bring all dispensed bottles to all study visits
- Patients who have consented to sampling for genetic research, will provide a blood sample Study Assessments and Procedures: Treatment Period (Visit 3, (Day 30: ±7 Days))

At Visit 3, the following assessments and procedures will be conducted:
- KCCQ and PGIS questionnaires will be completed
- NYHA Functional Classification will be evaluated and recorded
- Vital signs (BP, pulse) will be assessed and recorded
- Review and updating of concomitant medication and recording of relevant medications
- Review and recording of any cardiac and HF related procedures
- Review of potential efficacy and safety events.
- If the patient has experienced any potential endpoints, SAEs, DAEs and/or amputations, adverse events (AEs) leading to amputation and potential risk factor AEs for amputations affecting lower limbs since the last visit, this will be recorded in the eCRF
- Blood samples will be taken for creatinine (for calculation of eGFR) assessment (central laboratory).

Study Assessments and Procedures: Treatment Period (Visit 4, (Day 120: ±7 Days))

At Visit 4, the following assessments and procedures will be conducted:
- KCCQ and PGIS questionnaires will be completed
- NYHA Functional Classification will be evaluated and recorded
- Review and updating of concomitant medication and recording of relevant medications
- Review and recording of any cardiac and HF related procedures
- Review of potential efficacy and safety events.
- If the patient has experienced any potential endpoints, SAEs, DAEs and/or amputations, adverse events (AEs) leading to amputation and potential risk factor AEs for amputations affecting lower limbs since the last visit, this will be recorded in the eCRF.
- Blood samples will be taken for creatinine (for calculation of eGFR) assessment (central laboratory)
- IP will be dispensed via IxRS to the patient. Drug accountability of the returned IP will be checked. The patient will be instructed to take the IP in accordance with protocol and without interruptions.

Study Assessments and Procedures: Treatment Period (Visit 5. (Day 240: ±7 Days))

At Visit 5, the following assessments and procedures will be conducted:
- KCCQ, PGIS and EQ-5D-5L questionnaires will be completed
- NYHA Functional Classification will be evaluated and recorded
- Review and updating of concomitant medication and recording of relevant medications
- Review and recording of any cardiac and HF related procedures
- Review of potential efficacy and safety events
- If the patient has experienced any potential endpoints, SAEs, DAEs and/or amputations, adverse events (AEs) leading to amputation and potential risk factor AEs for amputations affecting lower limbs since the last visit, this will be recorded in the eCRF.
- IP will be dispensed via IxRS to the patient. Drug accountability of the returned IP will be checked. The patient will be instructed to take the IP in accordance with protocol and without interruptions.

Study Assessments and Procedures: Treatment Period (Visit 6, (Day 360: ±7 Days))

At Visit 6, the following assessments and procedures will be conducted:
- Vital signs (BP, pulse), and weight will be assessed and recorded
- Review and updating of concomitant medication and recording of relevant medications
- Review and recording of any cardiac and HF related procedures
- Review of potential efficacy and safety events.
- If the patient has experienced any potential endpoints, SAEs, DAEs and/or amputations, adverse events (AEs) leading to amputation and potential risk factor AEs for amputations affecting lower limbs since the last visit, this will be recorded in the eCRF.
- IP will be dispensed via IxRS to the patient. Drug accountability of the returned IP will be checked. The patient will be instructed to take the IP in accordance with protocol and without interruptions.
- Blood samples will be taken for creatinine (for calculation of eGFR) assessment (central laboratory)

Study Assessments and Procedures: Treatment Period (Visit 7 and Onwards, (Day 480 and Every 120 Days: ±14 Days))

At visit 7 and subsequent visits, the following assessments and procedures will be conducted:
- Vital signs (BP, pulse), and weight will be assessed and recorded every 12 months
- Review and updating of concomitant medication and recording of relevant medications
- Review and recording of any cardiac and HF related procedures
- Review of potential efficacy and safety events.

If the patient has experienced any potential endpoints, SAEs, DAEs and/or amputations, adverse events (AEs) leading to amputation and potential risk factor AEs for amputations affecting lower limbs since the last visit, this will be recorded in the eCRF.

IP will be dispensed via IxRS to the patient. Drug accountability of the returned IP will be checked. The patient will be instructed to take the IP in accordance with protocol and without interruptions.

Blood samples will be taken for creatinine (for calculation of eGFR) assessment (central laboratory) every 12 months.

Study Assessments and Procedures: Treatment Period (Study Closure Visit)

A primary analysis censoring date (PACD) will be declared based on the rate of accrued endpoints. A study closure visit (SCV) will be scheduled within 6 weeks of the PACD.

The patient will stop taking IP at the SCV. The following assessments and procedures will be conducted:

KCCQ, PGIS and EQ-5D-5L questionnaire will be completed

NYHA Functional Classification will be evaluated

A physical examination will be conducted

Vital signs (BP, pulse) and weight will be assessed and recorded.

Review and updating of concomitant medication and recording of relevant medications Review and recording of any cardiac and HF related procedures Review of potential efficacy and safety events If the patient has experienced any potential endpoints, SAEs, DAEs and/or amputations, adverse events (AEs) leading to amputation and potential risk factor AEs for amputations affecting lower limbs since the last visit, this will be recorded in the eCRF Drug accountability of the returned IP will be checked Study Assessments and Procedures: Efficacy Assessments (Clinical Outcome Assessments (COA))

A COA is any assessment that may be influenced by human choices, judgement, or motivation and may support either direct or indirect evidence of treatment benefit. Patient Reported Outcomes (PROs) is one of the types of COAs. A PRO is any report of the status of a patient's health condition that comes directly from the patient, without interpretation of anyone else. PROs have become a significant endpoint when evaluating benefit/risk of treatments in clinical trials. The following PROs will be collected: KCCQ, PGIS and EQ-5D-5L (see Appendix B, Appendix C, Appendix D).

Study Assessments and Procedures: Efficacy Assessments (COA: KCCQ)

The Kansas City Cardiomyopathy Questionnaire (KCCQ) is a 23-item, self-administered disease specific instrument and has shown to be a valid, reliable and responsive measure for patients with HF (Greene at al., JAMA Cardiol., 3(3): 252-59 (2018); Spertus et al., J Am Heart, 150(4)707-15 (2005)). The KCCQ was developed to independently measure the patient's perception of their health status, which includes heart failure-related symptoms (frequency, severity and recent change), impact on physical and social function, self-efficacy and knowledge, and how their heart failure impacts their quality of life (QOL). Scores are transformed to a range of 0-100. Higher scores represent a better outcome.

The KCCQ tool quantifies the following six (6) distinct domains and two (2) summary score KCCQ Symptom Domain quantifies the frequency and burden of clinical symptoms in heart failure, including fatigue, shortness of breath, paroxysmal nocturnal dyspnea and patients' edema/swelling. An overall symptom score is generally used in analyses; subscale scores for both frequency and severity are also available. The total symptom Score incorporates the symptom domains into a single score KCCQ Physical Function Domain measures the limitations patients experience, due to their heart failure symptoms, in performing routine activities. Activities are common, gender-neutral, and generalizable across cultures, while also capturing a range of exertional requirements KCCQ Quality of Life Domain is designed to reflect patients' assessment of their quality of life, given the current status of their heart failure KCCQ Social Limitation Domain quantifies the extent to which heart failure symptoms impair patients' ability to interact in a number of gender-neutral social activities KCCQ Self-efficacy Domain quantifies patients' perceptions of how to prevent heart failure exacerbations and manage complications when they arise. This scale is not included in the summary scores KCCQ Symptom Stability Domain measures recent changes in patients' symptoms; their shortness of breath, fatigue or swelling. It compares patients frequency of heart failure symptoms at the time of completing the KCCQ with their frequency 2 weeks ago. As a measure of change, it is most interpretable as a baseline assessment of the stability of patients' symptoms at the start of a study and shortly thereafter, as a measure of the acute response to treatment. This domain is not included in the summary scores.

Clinical Summary Score includes total symptom and physical function scores to correspond with NYHA Classification Overall Summary Score includes the total symptom, physical function, social limitations and quality of life scores Study Assessments and Procedures: Efficacy Assessments (COA: PGIS)

The PGIS item is included to assess how a patient perceives his/her overall current severity of heart failure symptoms. Patients will choose from response options from "no symptoms" to "very severe."

Study Assessments and Procedures: Efficacy Assessments (COA: EQ-5D-5L)

The EQ-5D-5L is a self-reported questionnaire that is used to derive a standardized measure of health status, also referred to as a utility score. EQ-5D-5L utility scores are widely accepted by reimbursement authorities and will be used to support health economic evaluations.

Study Assessments and Procedures: Safety Assessment (Physical Examinations)

A physical examination will be performed and include an assessment of the following: general appearance, respiratory and cardiovascular systems (including oedema) and abdomen.

The assessment dates will be recorded in the eCRF.

Study Assessments and Procedures: Safety Assessment (Vital Signs)

Pulse and BP will be measured at all applicable visits, and all measurements will be recorded in the eCRF.

Study Assessments and Procedures: Safety Assessment (Electrocardiogram)

A 12-lead ECG (standard ECG with a paper speed of 25-50 mm/second covering at least 6 sequential beats) will be recorded at baseline (Visit 1) after the patient has been lying down to rest for at least 5 minutes, to confirm presence or absence of atrial fibrillation/flutter at enrollment.

Study Assessments and Procedures: Safety Assessment (Safety Laboratory Assessments)

Serum creatinine will be collected for calculation of eGFR using CKD-EPI formula (Levey at al., Ann Intern Med, 150(9):604-12 (2009)).

Statistical Considerations: Statistical Hypotheses

For the primary and secondary endpoints, the following hypothesis will be tested at the 4.980% 2 sided level:

H0:HR [dapagliflozin:placebo]=1 versus

H1:HR [dapagliflozin:placebo]≠1.

Statistical Considerations: Statistical Analyses (Efficacy Analyses: Analysis of the Primary Variable)

The primary variable is the time from randomization to first event included in the primary composite endpoint. The primary analysis will be based on the ITT principle using the FAS, including events occurring on or prior to the PACD, adjudicated by the CEA committee.

In the analysis of the primary composite endpoint, treatments (dapagliflozin versus placebo) will be compared using a Cox proportional hazards model with a factor for treatment group, stratified by T2D status at randomization. The p-value, HR and 95% confidence interval will be reported.

The contribution of each component of the primary composite endpoint to the overall treatment effect will be examined. Methods similar to those described for the primary analysis will be used to separately analyze the time from randomization to the first occurrence of each component of the primary composite endpoint. HR and 95% confidence intervals will be reported.

Kaplan-Meier estimates of the cumulative incidence to the first occurrence of any event in the primary endpoint will be calculated and plotted, for overall analysis and for the individual components.

Statistical Considerations: Statistical Analyses (Efficacy Analyses: Analysis of the Secondary Variables)

The outcome of all HF hospitalizations (first and recurring) and CV death will be analyzed by the semi-parametric proportional rates model (Lin et al 2000) to test the treatment effect and to quantify the treatment difference. The rate ratio and its 95% confidence interval and corresponding two-sided p-value will be presented.

The proportion of patients with worsening NYHA classification from baseline to 8 months will be analyzed by a logistic regression with treatment group, baseline NYHA and T2D at randomization as factors. The odds ratio between treatment groups, its 95% confidence interval and corresponding two-sided p-value will be presented.

The analysis of change from baseline for KCCQ total symptom score at 8 months will be further detailed in the statistical analysis plan, e.g. with consideration of handling of patients who die. In addition to the secondary endpoint, total symptom score, the overall summary score, clinical summary score and domain scores will be analyzed. A responder analysis will also be performed (more details presented in the SAP).

The analysis of time from randomization to all-cause mortality will be analyzed in the similar manner as the primary variable.

Statistical Considerations: Statistical Analyses (Efficacy Analyses: Subgroup Analysis)

Subgroup variables for the primary efficacy endpoint include demography, baseline disease characteristics, baseline concomitant medications and others. Cox proportional hazard model stratified for T2D with factors for treatment group, the subgroup variable and the interaction between treatment and subgroup will be used to examine treatment effects within relevant subgroups separately. A test of interaction between randomised treatment group and the subgroup variable will be performed in each Cox model. The p-values for the subgroup analyses will not be adjusted for multiple comparisons as the tests are exploratory and will be interpreted descriptively. Treatment differences with 95% confidence intervals will be reported for each subgroup. HRs and CIs for overall analysis and subgroups will be presented with forest plots as well. Further details of the subgroup analysis, including the list of subgroup variables, will be provided in the SAP.

APPENDIX A

| | (NYHA Functional Classification) |
|---|---|
| Class | Patient symptoms |
| I | No limitation of physical activity. Ordinary physical activity does not cause undue fatigue, palpitation, dyspnoea (shortness of breath). |
| II | Slight limitation of physical activity. Comfortable at rest. Ordinary physical activity results in fatigue, palpitation, dyspnea (shortness of breath). |
| III | Marked limitation of physical activity. Comfortable at rest. Less than ordinary activity causes fatigue, palpitation, or dyspnea. |
| IV | Unable to carry on any physical activity without discomfort. Symptoms of heart failure at rest. If any physical activity is undertaken, discomfort increases. |

Appendix B (the KC Cardiomyopathy Questionnaire)

The KC Cardiomyopathy Questionnaire
The following questions refer to your heart failure and how it may affect your life. Please read and complete the following questions. There are no right or wrong answers. Please mark the answer that best applies to you.

1. Heart failure affects different people in different ways. Some feel shortness of breath while others feel fatigue. Please indicate how much you are limited by heart failure (shortness of breath or fatigue) in your ability to do the following activities over the past 2 weeks.
Place an X in one box on each line

| Activity | Extremely Limited | Quite a bit Limited | Moderately Limited | Slightly Limited | Not at all 1 Limited | Limited for other reasons or did not do the activity |
|---|---|---|---|---|---|---|
| Dressing yourself | ☐ | ☐ | ☐ | ☐ | ☐ | ☐ |
| Showering/Bathing | ☐ | ☐ | ☐ | ☐ | ☐ | ☐ |
| Walking 1 block on level ground | ☐ | ☐ | ☐ | ☐ | ☐ | ☐ |
| Doing yardwork, housework or carrying groceries | ☐ | ☐ | ☐ | ☐ | ☐ | ☐ |
| Climbing a flight of stairs without stopping | ☐ | ☐ | ☐ | ☐ | ☐ | ☐ |
| Hurrying or jogging (as if to catch a bus) | ☐ | ☐ | ☐ | ☐ | ☐ | ☐ |

2. Compared with 2 weeks ago, have your symptoms of heart failure (shortness of breath, fatigue, or ankle swelling) changed?
My symptoms of heart failure have become . . .

| Much worse | Slightly worse | Not changed | Slightly better | Much better | I've had no symptoms over the last 2 weeks |
|---|---|---|---|---|---|
| ☐ | ☐ | ☐ | ☐ | ☐ | ☐ |

3. Over the past 2 weeks, how many times did you have swelling in your feet, ankles or legs when you woke up in the morning?

| Every morning | 3 or more times a week, but not every day | 1-2 times a week | Less than once a week | Never over the past 2 weeks |
|---|---|---|---|---|
| ☐ | ☐ | ☐ | ☐ | ☐ |

4. Over the past 2 weeks, how much has swelling in your feet, ankles or legs bothered you?
It has been . . .

| Extremely bothersome | Quite a bit bothersome | Moderately bothersome | Slightly bothersome | Not at all bothersome | I've had no swelling |
|---|---|---|---|---|---|
| ☐ | ☐ | ☐ | ☐ | ☐ | ☐ |

5. Over the past 2 weeks, on average, how many times has fatigue limited your ability to do what you want?

| All of the time | Several times per day | At least once a day | 3 or more times per week but not every day | 1-2 times per week | Less than once a week | Never over the past 2 weeks |
|---|---|---|---|---|---|---|
| ☐ | ☐ | ☐ | ☐ | ☐ | ☐ | ☐ |

6. Over the past 2 weeks, how much has your fatigue bothered you?
It has been . . .

| Extremely bothersome | Quite a bit bothersome | Moderately bothersome | Slightly bothersome | Not at all bothersome | I've had no fatigue |
|---|---|---|---|---|---|
| ☐ | ☐ | ☐ | ☐ | ☐ | ☐ |

The KC Cardiomyopathy Questionnaire

The following questions refer to your heart failure and how it may affect your life. Please read and complete the following questions. There are no right or wrong answers. Please mark the answer that best applies to you.

7. Over the past 2 weeks, on average, how many times has shortness of breath limited your ability to do what you wanted?

| All of the time | Several times per day | At least once a day | 3 or more times per week but not every day | 1-2 times per week | Less than once a week | Never over the past 2 weeks |
|---|---|---|---|---|---|---|
| ☐ | ☐ | ☐ | ☐ | ☐ | ☐ | ☐ |

8. Over the past 2 weeks, how much has your shortness of breath bothered you? It has been . . .

| Extremely bothersome | Quite a bit bothersome | Moderately bothersome | Slightly bothersome | Not at all bothersome | I've had no shortness of breath |
|---|---|---|---|---|---|
| ☐ | ☐ | ☐ | ☐ | ☐ | ☐ |

9. Over the past 2 weeks, on average, how many times have you been forced to sleep sitting up in a chair or with at least 3 pillows to prop you up because of shortness of breath?

| Every night | 3 or more times per week, but not every day | 1-2 times a week | Less than once a week | Never over the past 2 weeks |
|---|---|---|---|---|
| ☐ | ☐ | ☐ | ☐ | ☐ |

10. Heart failure symptoms can worsen for a number of reasons. How sure are you that you know what to do, or whom to call, if your heart failure gets worse?

| Not at all sure | Not very sure | Somewhat sure | Mostly sure | Completely sure |
|---|---|---|---|---|
| ☐ | ☐ | ☐ | ☐ | ☐ |

11. How well do you understand what things you are able to do to keep your heart failure symptoms from getting worse? (for example, weighing yourself, eating a low salt diet etc.)

| Do not understand at all | Do not understand very well | Somewhat understand | Mostly understand | Completely understand |
|---|---|---|---|---|
| ☐ | ☐ | ☐ | ☐ | ☐ |

12. Over the past 2 weeks, how much has your heart failure limited your enjoyment of life?

| It has extremely limited my enjoyment of life | It has limited my enjoyment of life quite a bit | It has moderately limited my enjoyment of life | It has slightly limited my enjoyment of life | It has not limited my enjoyment of life at all |
|---|---|---|---|---|
| ☐ | ☐ | ☐ | ☐ | ☐ |

13. If you had to spend the rest of your life with your heart failure the way it is right now, how would you feel about this?

| Not at all satisfied | Mostly dissatisfied | Somewhat satisfied | Mostly satisfied | Completely satisfied |
|---|---|---|---|---|
| ☐ | ☐ | ☐ | ☐ | ☐ |

14. Over the past 2 weeks, how often have you felt discouraged or down in the dumps because of your heart failure?

| I felt that way all of the time | I felt that way most of the time | I occasionally felt that way | I rarely felt that way | I never felt that way |
|---|---|---|---|---|
| ☐ | ☐ | ☐ | ☐ | ☐ |

The KC Cardiomyopathy Questionnaire
The following questions refer to your heart failure and how it may affect your life. Please read and complete the following questions. There are no right or wrong answers. Please mark the answer that best applies to you.

15. How much does your heart failure affect your lifestyle? Please indicate how your heart failure may have limited your participation in the following activities over the past 2 weeks. Please place an X in one box on each line

| Activity | Severely limited | Limited quite a bit | Moderately limited | Slightly limited | Did not limit at all | Does not apply or did not do for other reasons |
|---|---|---|---|---|---|---|
| Hobbies, recreational activities | ☐ | ☐ | ☐ | ☐ | ☐ | ☐ |
| Working or doing household chores | ☐ | ☐ | ☐ | ☐ | ☐ | ☐ |
| Visiting family or friends out of your home | ☐ | ☐ | ☐ | ☐ | ☐ | ☐ |
| Intimate relationships with loved ones | ☐ | ☐ | ☐ | ☐ | ☐ | ☐ |

Copyright @ 1992-2005 John Spertus, MD, MPH                                Original US English Appendix C (EQ-5D-5L Questionnaire)

5Q-5D-5L Health Questionnaire
Under each heading, please check the ONE box that best describes your health TODAY

MOBILITY

I have no problems walking ☐
I have slight problems walking ☐
I have moderate problems walking ☐
I have severe problems walking ☐
I am unable to walk ☐
SELF-CARE I have no problems washing or dressing myself ☐
I have slight problems washing or dressing myself ☐
I have moderate problems washing or dressing myself ☐
I have severe problems washing or dressing myself ☐
I am unable to wash or dress myself ☐
USUAL ACTIVITIES (e.g. work, study, housework, family or leisure activities)

I have no problems doing my usual activities ☐
I have slight problems doing my usual activities ☐
I have moderate problems doing my usual activities ☐
I have severe problems doing my usual activities ☐
I am unable to do my usual activities ☐
PAIN/DISCOMFORT I have no pain or discomfort ☐
I have slight pain or discomfort ☐
I have moderate pain or discomfort ☐
I have severe pain or discomfort ☐
I have extreme pain or discomfort ☐
ANXIETY / DEPRESSION I am not anxious or depressed ☐
I am slightly anxious or depressed ☐
I am moderately anxious or depressed ☐
I am severely anxious or depressed ☐
I am extremely anxious or depressed ☐

We would like to know how good or bad your health is TODAY.
This scale is numbered from 0 to 100.
100 means the best health you can imagine. 0 means the worst health you can imagine.
Mark an X on the scale to indicate how your health is TODAY.

YOUR HEALTH TODAY=☐

USA (English) ©2009 EuroQol Group. EQ-5D™ is a trade mark of the EuroQol Group

Appendix D (Patient Global Impression of Severity for Heart Failure Symptoms)

Patient Global Impression of Severity for Heart Failure Symptoms

| Overall, how would you rate the severity of your heart failure symptoms today? | |
|---|---|
| ☐ | No symptoms |
| ☐ | Very mild |
| ☐ | Mild |
| ☐ | Moderate |
| ☐ | Severe |
| ☐ | Very Severe |

What is claimed is:

1. A method for (i) treating heart failure with preserved ejection fraction (HFpEF) and/or (ii) treating and/or preventing at least one disease, disorder, or condition associated with HFpEF, the method comprising administering to a non-diabetic patient in need thereof a pharmaceutical composition comprising a therapeutically effective amount of at least one compound chosen from compounds of Formula (I)

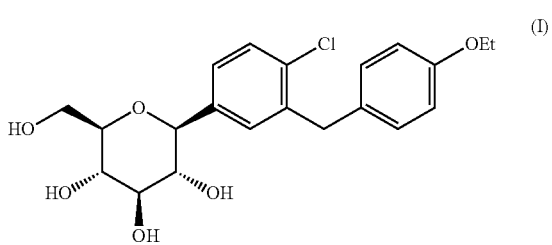 [SMILES: CCOc1ccc(Cc2cc([C@@H]3O[C@H](CO)[C@@H](O)[C@H](O)[C@H]3O)ccc2Cl)cc1]

and prodrugs thereof,
wherein the at least one disease, disorder, or condition associated with HFpEF is chosen from skeletal muscle dysfunction, vascular dysfunction, hypertension, pulmonary hypertension, renal failure, anemia, atrial fibrillation, and major adverse cardiovascular events, and
wherein the non-diabetic patient is human, has a body mass index of <50 kg/m$^2$, has HFpEF, and has hemoglobin A1c of <5.7%.

2. The method of claim 1, wherein the method is a method for treating HFpEF.

3. The method of claim 1, wherein the pharmaceutical composition further comprises at least one other therapeutic agent.

4. The method of claim 1, wherein the major adverse cardiovascular event is chosen from myocardial infarction, stroke, cardiovascular death, and cardiovascular hospitalization.

5. The method of claim 4, wherein the cardiovascular hospitalization is related to unstable or stable angina pectoris, heart failure, and/or coronary revascularization.

6. The method of claim 1, wherein the non-diabetic patient satisfies at least one of the following conditions:
(a) the non-diabetic patient is ≥40 years old;
(b) the non-diabetic patient has documented diagnosis of symptomatic heart failure NYHA class II-IV prior to treatment;
(c) the non-diabetic patient has a medical history of symptoms and/or signs of heart failure ≥6 weeks with at least intermittent need for diuretic treatment prior to treatment;
(d) the non-diabetic patient has evidence of structural heart disease that is documented by echocardiogram and/or cardiac magnetic resonance imaging within 12 months prior to treatment; or
(e) the non-diabetic patient has NT-proBNP of ≥300 pg/ml without ongoing atrial fibrillation/flutter or has NT-proBNP of ≥600 pg/ml with ongoing atrial fibrillation/flutter prior to treatment.

7. The method of claim 6, wherein at least one symptom and/or sign of heart failure is chosen from breathlessness, orthopnoea, paroxysmal nocturnal dyspnoea, reduced exercise tolerance, fatigue, tiredness, increased time to recover after exercise, ankle swelling, elevated jugular venous pressure, hepatojugular reflex, third heart sound, laterally displaced apical impulse, >2 kg weight gain per week, weight loss in advanced HF, cachexia, reduced appetite cardiac murmur, peripheral oedema, pulmonary crepitations, reduced air entry and dullness to percussion at lung bases, tachycardia, irregular pulse, tachypnoea, cheyne stokes respiration, hepatomegaly, ascites, cold extremities, oliguria, and/or narrow pulse pressure.

8. The method of claim 6, wherein the non-diabetic patient satisfies each of conditions (a) through (e) of claim 6.

9. The method of claim 1, wherein the non-diabetic patient satisfies at least one of the following conditions:
(a) the non-diabetic patient has not received intravenous heart failure therapy, including diuretics, for at least 12 hours prior to treatment;
(b) the non-diabetic patient has not received therapy with an SGLT2 inhibitor within 4 weeks prior to treatment;
(c) the non-diabetic patient does not have eGFR<25 mL/min/1.73 m$^2$;
(d) the non-diabetic patient does not have systolic blood pressure (BP)<95 mmHg on 2 consecutive measurements at 5-minute intervals prior to treatment;
(e) the non-diabetic patient does not have systolic BP≥160 mmHg if not on treatment with ≥3 blood pressure lowering medications or ≥180 mmHg irrespective of treatments, on 2 consecutive measurements at 5-minute intervals prior to treatment;
(f) the non-diabetic patient has not had a myocardial infarction, unstable angina, coronary revascularization, ablation of atrial flutter/fibrillation, or valve repair/replacement within 12 weeks prior to treatment;
(g) the non-diabetic patient does not have planned coronary revascularization, ablation of atrial flutter/fibrillation or valve repair/replacement;
(h) the non-diabetic patient has not had a stroke or transient ischemic attack within 12 weeks prior to treatment;
(i) the non-diabetic patient does not have probable alternative or concomitant diagnoses which in the opinion of the treating physician could account for the patient's HF symptoms and signs;
(j) the non-diabetic patient does not have primary pulmonary hypertension, chronic pulmonary embolism, severe pulmonary disease;
(k) the non-diabetic patient does not have HF due to known infiltrative cardiomyopathy, active myocarditis, constrictive pericarditis, cardiac tamponade, known genetic hypertrophic cardiomyopathy or obstructive hypertrophic cardiomyopathy, arrhythmogenic right ventricular cardiomyopathy/dysplasia, or uncorrected primary valvular disease;
(l) the non-diabetic patient does not have a life expectancy of less than 2 years due to any non-cardiovascular condition, based on the treating physician's clinical judgement;
(m) the non-diabetic patient does not have active malignancy requiring treatment (with the exception of basal cell or squamous cell carcinomas of the skin); or
(n) the non-diabetic patient does not have acute or chronic liver disease with severe impairment of liver function.

10. The method of claim 9, wherein the non-diabetic patient satisfies each of conditions (a) through (n) of claim 9.

11. The method of claim 1, wherein the non-diabetic patient has left ventricular ejection fraction of ≥45%.

12. The method of claim 1, wherein the method reduces the occurrence of CV death compared to placebo.

13. The method of claim 1, wherein the method reduces the occurrence of hospitalization for HF compared to placebo.

14. The method of claim 1, wherein the method reduces the occurrence of an urgent HF visit compared to placebo.

15. The method of claim 1, wherein the method reduces the total number of hospitalizations for HF and CV death compared to placebo.

16. The method of claim 15, wherein the total number of hospitalizations is for first and/or recurrent hospitalizations.

17. The method of claim 1, wherein the method improves one or more of the patient reported outcomes measured by KCCQ.

18. The method of claim 1, wherein the method improves the NYHA class of the patient from baseline.

19. The method of claim 1, wherein the method reduces the occurrence of death from any cause compared to placebo.

20. The method of claim 1, wherein the method reduces the occurrence of hospitalization from any cause compared to placebo.

21. The method of claim 1, wherein the method improves the health status of the patient assessed by EQ-5D-5L questionnaire.

22. The method of claim 1, wherein the method improves the health status of the patient assessed by PGIS questionnaire.

23. The method of claim 1, wherein the method does not reduce eGFR of the patient from baseline.

24. The method of claim 1, wherein the method improves the change in eGFR from baseline compared to placebo.

25. The method of claim 1, wherein the method comprises administering the pharmaceutical composition in addition to standard of care therapy.

26. The method of claim 25, wherein the standard of care therapy comprises treatments to control co-morbidities and/or treatments for reducing the composite of CV death and heart failure events.

27. The method of claim 26, wherein the heart failure events are chosen from hospitalization for HF and/or urgent HF visits.

* * * * *